US012702836B2

(12) United States Patent
Hageman et al.

(10) Patent No.: US 12,702,836 B2
(45) Date of Patent: Aug. 11, 2026

(54) EVOKED SIGNAL BASED DEEP BRAIN STIMULATION (DBS) PROGRAMMING

(71) Applicant: Medtronic, Inc., Minneapolis, MN (US)

(72) Inventors: Kristin N. Hageman, Dayton, MN (US); Scott R. Stanslaski, Shoreview, MN (US); Erik J. Peterson, Fridley, MN (US); Rene A. Molina, Maple Grove, MN (US); Paul H. Stypulkowski, North Oaks, MN (US); David A. Dinsmoor, North Oaks, MN (US); Leonid M. Litvak, Bet Shemesh (IL); Michelle A. Case, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 667 days.

(21) Appl. No.: 18/051,421

(22) Filed: Oct. 31, 2022

(65) Prior Publication Data

US 2023/0166111 A1 Jun. 1, 2023

Related U.S. Application Data

(60) Provisional application No. 63/284,350, filed on Nov. 30, 2021.

(51) Int. Cl.
*A61N 1/36* (2006.01)
*A61N 1/05* (2006.01)

(52) U.S. Cl.
CPC ....... *A61N 1/36139* (2013.01); *A61N 1/0534* (2013.01); *A61N 1/36146* (2013.01)

(58) Field of Classification Search
CPC .............. A61N 1/36139; A61N 1/0534; A61N 1/36146; A61N 1/36185; A61N 1/36171;
(Continued)

(56) References Cited

U.S. PATENT DOCUMENTS 8,914,119 B2 12/2014 Wu et al.
9,364,672 B2 6/2016 Marnfeldt
(Continued)

FOREIGN PATENT DOCUMENTS

EP 3784338 A1 3/2021
EP 3787495 A1 3/2021
(Continued)

OTHER PUBLICATIONS

N. Maling, C. McIntyre, "Chapter 5—Local Field Potential Analysis for Closed-Loop Neuromodulation," Editor(s): Ahmed El Hady, Closed Loop Neuroscience, Academic Press, 2016, pp. 67-80, Abstract, https://www.sciencedirect.com/science/article/pii/B9780128024522000056, accessed Jun. 2, 2025 (Year: 2016).*
(Continued)

*Primary Examiner* — Jennifer Pitrak McDonald
*Assistant Examiner* — Christopher J Mutchler
(74) *Attorney, Agent, or Firm* — Shumaker & Sieffert, P.A.

(57) ABSTRACT

A system includes memory and processing circuitry coupled to the memory and configured to determine a plurality of local field potential (LFP) measurements of an LFP, wherein the LFP is intrinsically generated by a signal source within a brain of a patient, determine one or more electrodes for delivering a therapeutic electrical stimulation signal based on the LFP measurements, control stimulation generation circuitry to deliver a plurality of electrical stimulation signals via the determined one or more electrodes, wherein the plurality of electrical stimulation signals each comprise at least one different therapy parameter, for respective ones of the plurality of electrical stimulation signals, determine respective evoked signals, wherein the respective evoked signals are evoked by delivery of the respective plurality of electrical stimulation signals, and determine at least one
(Continued)

parameter for the therapeutic electrical stimulation signal based on the respective evoked signals.

19 Claims, 12 Drawing Sheets

(58) Field of Classification Search
CPC ............ A61N 1/36175; A61N 1/36135; A61N 1/36067; A61B 2562/0219; A61B 5/37; A61B 5/383; A61B 5/4836; A61B 5/686; A61B 5/6868
See application file for complete search history.

(56) References Cited

U.S. PATENT DOCUMENTS

| | | | |
|---|---|---|---|
| 9,381,356 B2 | 7/2016 | Parker et al. | |
| 10,016,370 B2 | 7/2018 | Xia | |
| 10,463,860 B2 | 11/2019 | Sinclair et al. | |
| 10,688,306 B2 | 6/2020 | Strother et al. | |
| 10,849,525 B2 | 12/2020 | Parker et al. | |
| 10,953,025 B2 | 3/2021 | Xia | |
| 2014/0135869 A1 | 5/2014 | Carlson et al. | |
| 2016/0287126 A1 | 10/2016 | Parker et al. | |
| 2017/0259064 A1* | 9/2017 | Wu | A61N 1/0534 |
| 2018/0132747 A1 | 5/2018 | Parker et al. | |
| 2018/0133459 A1 | 5/2018 | Parker et al. | |
| 2018/0333582 A1 | 11/2018 | Grill et al. | |
| 2019/0381317 A1 | 12/2019 | Sinclair et al. | |
| 2019/0381318 A1 | 12/2019 | Sinclair et al. | |
| 2020/0038660 A1* | 2/2020 | Torgerson | A61B 5/4836 |
| 2020/0129757 A1 | 4/2020 | Xiao et al. | |
| 2020/0138324 A1 | 5/2020 | Sinclair et al. | |
| 2020/0215331 A1 | 7/2020 | Single | |
| 2020/0269054 A1 | 8/2020 | Dearden et al. | |
| 2020/0337645 A1 | 10/2020 | Kremen et al. | |
| 2021/0154476 A1 | 5/2021 | Senderowicz et al. | |
| 2021/0196964 A1 | 7/2021 | Schnell et al. | |
| 2021/0228880 A1 | 7/2021 | Machado et al. | |

FOREIGN PATENT DOCUMENTS

| | | | | |
|---|---|---|---|---|
| WO | 2019/204884 A1 | 10/2019 | | |
| WO | 2019/210371 A1 | 11/2019 | | |
| WO | 2021/022332 A1 | 2/2021 | | |
| WO | WO-2021146774 A1 * | 7/2021 | | A61N 1/36139 |

OTHER PUBLICATIONS

A. R. Kent and W. M. Grill, "Instrumentation to record evoked potentials for closed-loop control of deep brain stimulation," 2011 Annual International Conference of the IEEE Engineering in Medicine and Biology Society, Boston, MA, USA, 2011, pp. 6777-6780, (Year: 2011).*

Alexis M. Kuncel, Warren M. Grill, "Selection of stimulus parameters for deep brain stimulation," Clinical Neurophysiology 115 (2004) 2431-2441. (Year: 2004).*

Zhang S, Connolly AT, Madden LR, Vitek JL, Johnson MD. High-resolution local field potentials measured with deep brain stimulation arrays. J Neural Eng. Aug. 2018;15(4):046019. doi: 10.1088/1741-2552/aabdf5. Epub Apr. 13, 2018. PMID: 29651998; PMCID: PMC6021212. (Year: 2018).*

Baker et al., "Subthalamic Nucleus Deep Brain Stimulus Evoked Potentials: Physiological and Therapeutic Implications," Wiley InterScience, Movement Disorders, vol. 17, No. 5, Feb. 12, 2002, pp. 969-983.

International Search Report and Written Opinion of International Application No. PCT/IB2022/060978 dated Feb. 10, 2023, 18 pp.

Irwin et al., "Latency of subthalamic nucleus deep brain stimulation-evoked cortical activity as a potential biomarker for postoperative motor side effects," Clinical Neurophysiology, vol. 131, No. 6, doi: 10.1016/j.clinph.2020.02.021, Jun. 2020, pp. 1221-1229.

Miocinovic et al., "Cortical Potentials Evoked by Subthalamic stimulation Demonstrate a Short Latency Hyperdirect Pathway in Humans," The Journal of Neuroscience, vol. 38, No. 43, doi:10.1523/JNEUROSCI.1327-18.2018, Oct. 24, 2018, pp. 9129-9141.

Ozturk et al., "Electroceutically induced subthalamic high-frequency oscillations and evoked compound activity may explain the mechanism of therapeutic stimulation in Parkinson's disease," Communications Biology, vol. 4, No. 393, doi.org/10.1038/s42003-021-01915-7, Mar. 2021, 14 pp.

Schmidt et al., "Evoked potentials reveal neural circuits engaged by human deep brain stimulation," Brain Stimulation, vol. 13, doi.org/10.1016/j.brs.2020.09.028, Oct. 6, 2020, pp. 1706-1718.

Sinclair et al., "Deep brain stimulation for Parkinson's disease modulates high-frequency evoked and spontaneous neural activity," Neurobiology of Disease, vol. 130, No. 104522, doi: 10.1016/j.nbd.2019.104522, Oct. 1, 2019, 21 pp.

Sinclair et al., "Subthalamic Nucleus Deep Brain Stimulation Evokes Resonant Neural Activity," Annals of Neurology, vol. 83, No. 5, doi: 10.1002/ana.25234, May 2018, pp. 1027-1031.

Thevathasan et al., "Tailoring Subthalamic Nucleus Deep Brain Stimulation for Parkinson's Disease Using Evoked Resonant Neural Activity," Frontiers in Human Neuroscience, vol. 14, Article 71, doi: 10.3389/fnhum.2020.00071, Feb. 28, 2020, 6 pp.

Walker et al., "Activation of subthalamic neurons by contralateral subthalamic deep brain stimulation in Parkinson disease," Journal of Neurophysiology, vol. 105, No. 5, doi: 10.1152/jn.00266.2010, Dec. 22, 2010, pp. 1112-1121.

Wiest et al., "Local field potential activity dynamics in response to deep brain stimulation of the subthalamic nucleus in Parkinson's disease," Neurobiology of Disease, vol. 143, No. 105019, doi.org/10.1016/j.nbd.2020.105019, Jul. 11, 2020, 15 pp.

* cited by examiner

| | |
|---|---|
| E0 | 0.232 μVpeak |
| E1 | 1.146 μVpeak |
| E2 | 0 μVpeak |
| E3 | 0.1587 μVpeak |

FIG. 6A

| | |
|---|---|
| E1a | 0.5064 μVpeak |
| E1b | 0.6074 μVpeak |
| E1c | 2.48 μVpeak |
| E2a | 0 μVpeak |
| E2b | 0.1813 μVpeak |
| E2c | 0.09878 μVpeak |

FIG. 6B

Sense E3

100
0
-100
Voltage (uV)
0 10 20 30
Time (ms)

Sense E2a 100
0
-100
Voltage (uV)
0 10 20 30
Time (ms)

Sense E2b 100
0
-100
Voltage (uV)
0 10 20 30
Time (ms)

Sense E2c 100
0
-100
Voltage (uV)
0 10 20 30
Time (ms)

Sense E1a 100
0
-100
Voltage (uV)
0 10 20 30
Time (ms)

Sense E1b 100
0
-100
Voltage (uV)
0 10 20 30
Time (ms)

EVOKED SIGNAL BASED DEEP BRAIN STIMULATION (DBS) PROGRAMMING

This application claims the benefit of U.S. Provisional Patent Application No. 63/284,350, filed Nov. 30, 2021, the entire contents of which is incorporated herein by reference.

TECHNICAL FIELD

This disclosure generally relates to electrical stimulation therapy.

BACKGROUND

Medical devices may be external or implanted, and may be used to deliver electrical stimulation therapy to various tissue sites of a patient to treat a variety of symptoms or conditions such as chronic pain, tremor, Parkinson's disease, other movement disorders, epilepsy, urinary or fecal incontinence, sexual dysfunction, obesity, or gastroparesis. A medical device delivers electrical stimulation therapy via one or more leads that include electrodes located proximate to target locations associated with the brain, the spinal cord, pelvic nerves, peripheral nerves, or the gastrointestinal tract of a patent. For bipolar stimulation, the electrodes used for stimulation may be on one or more leads. For unipolar stimulation, the electrodes may be on one or more leads, and an electrode on a stimulator housing located remotely from the target site (e.g., near clavicle). It may be possible to use leadless stimulation using electrodes mounted on the stimulation housing. Hence, electrical stimulation is used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes for delivery of the stimulation, a polarity of each selected electrode, a voltage or current pulse amplitude, a pulse width, and a pulse frequency as parameters. A set of parameters, such as a set including electrode combination, electrode polarity, amplitude, pulse width, and pulse rate, may be referred to as a program in the sense that they define the electrical stimulation therapy to be delivered to the patient.

SUMMARY

This disclosure describes example techniques for processing circuitry to utilize a combination of local field potential (LFP) measurements and evoked signals to determine which electrodes to use for delivering therapeutic electrical stimulation and the parameters of the therapeutic electrical stimulation signal. There may be two examples of evoked signals: evoked potential signals and evoked resonant neural activity (ERNA) signals.

An LFP may be from an intrinsic signal generated within a brain of a patient. That is, the LFP is present without being evoked by delivery of an electrical stimulation. In some examples, the LFP is generated due to a signal source (e.g., oscillatory signal source) within the brain of the patient. An evoked signal, on the other hand, is a signal that the brain generates (i.e., evokes) in response to an electrical stimulation signal. That is, the evoked signal is not present until after electrical stimulation has been delivered. In some examples, the processing circuitry may utilize the evoked signals to determine which electrodes to use for sensing.

An evoked potential signal may be an evoked signal that is evoked in response to a low frequency stimulation signal, including examples where the stimulation signal is a single stimulation pulse. The evoked potential signal tends to dampen out over time. Therefore, if the frequency of the stimulation signal used to evoke a signal is sufficiently low (e.g., including a single stimulation pulse), the evoked potential signal dampens out before a subsequent stimulation signal. In this example, the evoked signal that is sensed is the evoked potential signal.

An ERNA signal may be a combination of a plurality of evoked potential signals. For instance, if the frequency of the stimulation signal is sufficiently high, then a current evoked potential signal may not dampen out before a subsequent stimulation pulse of the stimulation signal causes a subsequent evoked potential signal. In this case, the current evoked potential and the subsequent evoked potential signal may interfere constructively (e.g., adding together) or destructively (e.g., subtracting from one another). The resulting evoked signal may be an example of ERNA. The above example uses two evoked potential signals to form an ERNA signal. In some examples, there may be a plurality of evoked potential signals that together form the ERNA signal.

In one or more examples, processing circuitry may determine which one or more electrodes on a lead implanted within the brain of the patient to use for stimulation based on LFP measurements measured with different electrodes on the lead. The processing circuitry may control stimulation generation circuitry to deliver a plurality of electrical stimulation signals via the determined one or more electrodes, where the at least one therapy parameter of the plurality of electrical stimulation signals is different (e.g., the frequency of each of the plurality of electrical stimulation signals is different, the amplitude of the plurality of electrical stimulation signals is different, or the pulse width of the plurality of electrical stimulation signals is different). That is, (1) a frequency of a first electrical stimulation signal of the plurality of electrical stimulation signals is different than a frequency of a second electrical stimulation signal of the plurality of electrical stimulation signals, (2) an amplitude of a first electrical stimulation signal of the plurality of electrical stimulation signals is different than an amplitude of a second electrical stimulation signal of the plurality of electrical stimulation signals, or (3) a pulse width of a first electrical stimulation signal of the plurality of electrical stimulation signals is different than a pulse width of a second electrical stimulation signal of the plurality of electrical stimulation signals. The processing circuitry may determine respective evoked signals for respective ones (e.g., each) of the electrical stimulation signals (e.g., determine a first evoked signal in response to delivery of the first electrical stimulation signal, determine a second evoked signal in response to delivery of the second electrical stimulation signal, and so forth).

The processing circuitry may evaluate the respective evoked signals to determine at least one parameter (e.g., determine the values of one or more parameters) for a therapeutic electrical stimulation signal. For instance, the processing circuitry may select one of the respective evoked signals based on characteristics of the respective evoked signals (e.g., amplitude, frequency, damping, etc.), and determine the electrical stimulation signal, of the plurality of electrical stimulation signals, that generated the selected evoked signal. The processing circuitry may determine the parameters of the determined electrical stimulation signal that evoked the evoked signal, and use the determined parameters to determine the parameters of the therapeutic electrical stimulation signal. In this way, the example techniques may automate determination of parameters (e.g., for clinician/surgeon approval), rather than titrating and relying on patient feedback for determining parameters.

In one example, this disclosure describes a system for therapy parameter determination, the system comprising: memory; and processing circuitry coupled to the memory and configured to: determine a plurality of local field potential (LFP) measurements of an LFP, wherein the LFP is intrinsically generated by a signal source within a brain of a patient; determine one or more electrodes for delivering a therapeutic electrical stimulation signal based on the LFP measurements; control stimulation generation circuitry to deliver a plurality of electrical stimulation signals via the determined one or more electrodes, wherein the plurality of electrical stimulation signals each comprise at least one different therapy parameter; for respective ones of the plurality of electrical stimulation signals, determine respective evoked signals, wherein the respective evoked signals are evoked by delivery of the respective plurality of electrical stimulation signals; determine at least one parameter for the therapeutic electrical stimulation signal based on the respective evoked signals; and output information indicative of the determined at least one parameter.

In one example, this disclosure describes a method for therapy parameter determination, the method comprising: determining a plurality of local field potential (LFP) measurements of an LFP, wherein the LFP is intrinsically generated by a signal source within a brain of a patient; determining one or more electrodes for delivering a therapeutic electrical stimulation signal based on the LFP measurements; controlling stimulation generation circuitry to deliver a plurality of electrical stimulation signals via the determined one or more electrodes, wherein the plurality of electrical stimulation signals each comprise at least one different therapy parameter; for respective ones of the plurality of electrical stimulation signals, determining respective evoked signals, wherein the respective evoked signals are evoked by delivery of the respective plurality of electrical stimulation signals; determining at least one parameter for the therapeutic electrical stimulation signal based on the respective evoked signals; and outputting information indicative of the determined at least one parameter.

In one example, the disclosure describes a computer-readable storage medium storing instructions thereon that when executed cause one or more processors to: determine a plurality of local field potential (LFP) measurements of an LFP, wherein the LFP is intrinsically generated by a signal source within a brain of a patient; determine one or more electrodes for delivering a therapeutic electrical stimulation signal based on the LFP measurements; control stimulation generation circuitry to deliver a plurality of electrical stimulation signals via the determined one or more electrodes, wherein the plurality of electrical stimulation signals each comprise at least one different therapy parameter; for respective ones of the plurality of electrical stimulation signals, determine respective evoked signals, wherein the respective evoked signals are evoked by delivery of the respective plurality of electrical stimulation signals; determine at least one parameter for the therapeutic electrical stimulation signal based on the respective evoked signals; and output information indicative of the determined at least one parameter.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

FIGS. 6A and 6B are conceptual diagrams illustrating examples of local field potential (LFP) measurements from different electrodes.

DETAILED DESCRIPTION

Figure 1:
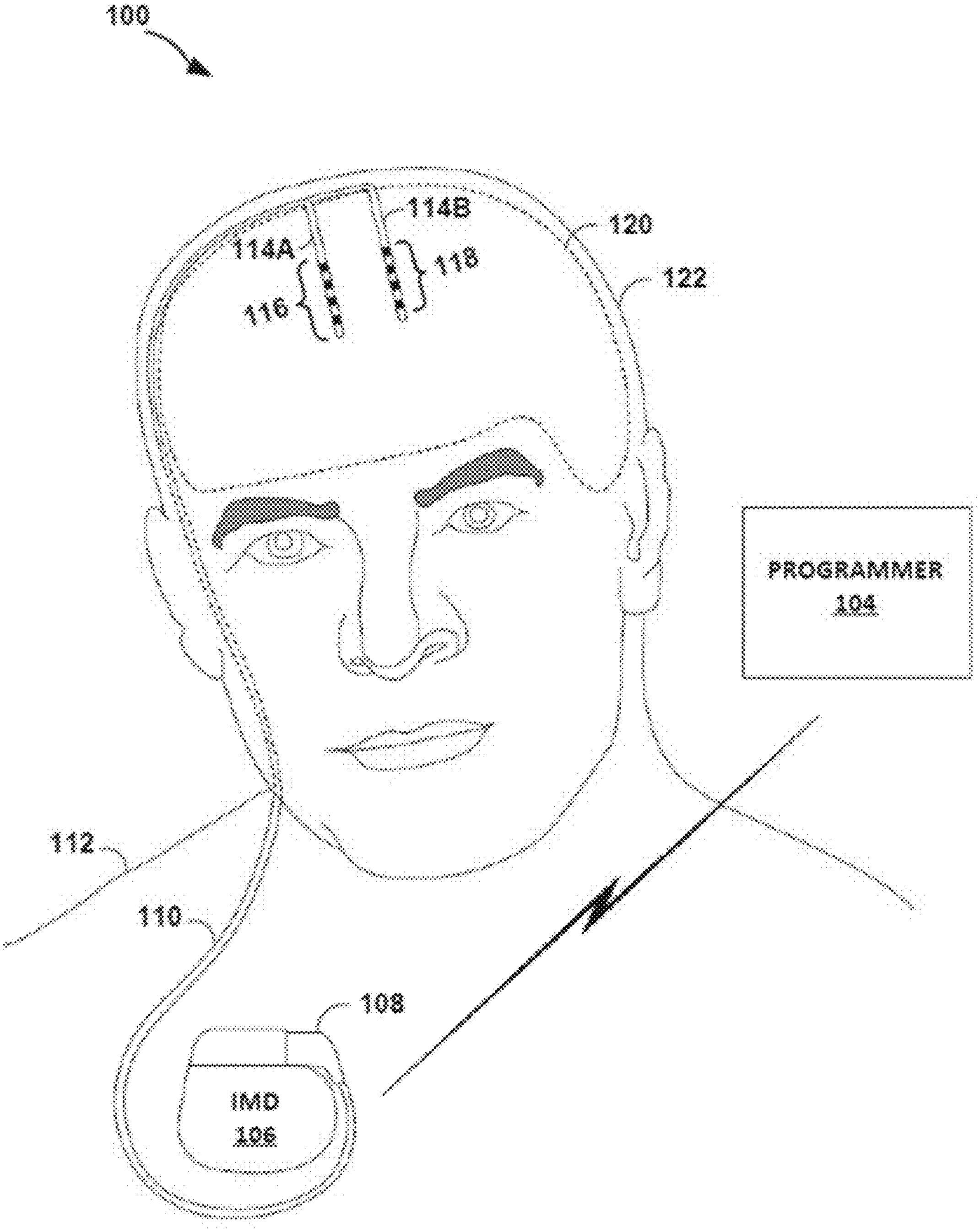
FIG. 1 is a conceptual diagram illustrating an example system that includes an implantable medical device (IMD) configured to deliver deep brain stimulation (DBS) to a patient according to an example of the techniques of the disclosure.

This disclosure describes example techniques to automatically determine parameters for a therapeutic electrical stimulation signal. The example techniques are described with respect to deep brain stimulation (DBS), but the example techniques are not so limited and may be applied to other types of therapies and/or other anatomical locations. DBS may provide relief for many different patient conditions such as essential tremors (ETs), Parkinson's, obsessive compulsive disorder (OCD), depression, and others. For DBS, a surgeon implants one or more leads within the brain of the patient for outputting electrical stimulation at depth within the brain.

After implantation, the surgeon/clinician may be tasked with determining which electrodes to use for delivering the therapeutic electrical stimulation, and what the parameters should be for the therapeutic electrical stimulation. Determination of the electrodes and the parameters can be time consuming, imprecise, and require patient feedback.

This disclosure describes example techniques to automate the determination of which electrodes to use for stimulation and the parameters for the therapeutic electrical stimulation to reduce the burden of manual determination of which electrode to use for stimulation and the determination of the parameters. For instance, in accordance with one or more examples described in this disclosure, the processing circuitry may be configured to utilize local field potential (LFP) measurements to determine which electrode(s) to use for stimulation, and rely upon evoked signals to determine parameters for the therapeutic electrical stimulation signal.

However, in some examples, it may be possible to use evoked signals to determine which electrode(s) to use for stimulation, or utilize the evoked signals to confirm that the electrodes selected using the LFP measurements are the correct electrodes to use. For example, the processing circuitry may sense evoked signals on a plurality of pairs of electrodes to determine which electrodes are proximate to the signal source (e.g., based on amplitude or other signal characteristics of the evoked signals). The processing circuitry may determine whether the pairs of electrodes that are proximate to the signal source, as determined using evoked signals, are the same as the electrodes selected to be used for stimulation using the LFP measurements, such as for confirmation. If the electrodes selected using the LFP measurements for stimulation and the electrodes determined using evoked signals for stimulation are different, the processing circuitry may utilize some confidence scoring to determine whether to use the electrodes determined from LFP measurements or evoked signals. As another example, the processing circuitry may select a pair of electrodes, to be used for stimulation, that are equally proximate to both the electrodes determined using LFP measurement and electrodes determine using evoked signals. Other ways in which to select which electrodes to use for stimulation if the electrodes selected using LFP measurements and the electrodes selected using evoked signals are different.

As described above, an LFP may be an intrinsic signal within the brain of the patient. In some cases, the LFP is intrinsically generated by a signal source within the brain of the patient. The signal characteristics of the LFP may be indicative of a patient condition.

An evoked signal is not an intrinsic signal within the brain of the patient, but is evoked due to a stimulation signal being delivered to the brain. The stimulation signal delivered to the brain that evokes the evoked signal need not necessarily provide any therapeutic benefit, although it is possible for the stimulation signal that evokes the evoked signal to provide therapeutic benefit.

As described above, there may be two examples of evoked signals: evoked potential signals, and evoked resonant neural activity (ERNA) signals. Evoked potential signals may be the result of a stimulation signal have a relatively low frequency, including examples where the stimulation signal includes a single pulse and does not repeat. For instance, the stimulation signal may include a plurality of stimulation pulses. For a stimulation signal having a frequency less than 80 Hz, the resulting evoked signals may be referred to evoked potential signals. With a frequency of less than 80 Hz, an evoked potential signal evoked due to a current stimulation pulse may dampen out before a subsequent evoked potential signal is evoked due to a subsequent stimulation pulse. Therefore, the sensed evoked signal may be the evoked potential signal.

ERNA signals may be the result of a stimulation signal having a higher frequency compared to a stimulation signal used to evoke evoked potential signals. For instance, if the frequency of the stimulation signal is greater than 80 Hz, the resulting evoked signals may be referred to as ERNA signals. With a frequency greater than 80 Hz, an evoked potential signal evoked due to a current stimulation pulse may remain when a subsequent evoked potential signal is evoked due to a subsequent stimulation pulse. Therefore, the sensed evoked signal may be a combination (e.g., constructive or destructive combination) of the evoked potential signal and the subsequent evoked potential signal. In such examples, the sensed evoked signal may be an ERNA signal because the sensed evoked signal is a combination of two or more evoked potential signals.

It should be understood that 80 Hz is provided above as one example to differentiate between evoked potential signals and ERNA signals. However, the example techniques are not so limited. In general, there may be a threshold frequency (e.g., approximately 80 Hz), and evoked signals that are evoked due to stimulation signal having frequency below the threshold frequency may be considered as evoked potential signals, and evoked signals that are evoked due to stimulation having frequency above the threshold frequency may be considered as ERNA signals.

In some examples, the processing circuitry may determine which electrodes to use for delivering the therapeutic electrical stimulation signal. The processing circuitry may be configured to determine which electrode(s) on a lead are most proximal to a signal source that is generating the LFP, as one example way of determining which electrodes to use for delivering the therapeutic electrical stimulation signal. As described in more detail, as one non-limiting example way to determine the electrodes on the lead that are used for delivery of therapeutic electrical stimulation signal is to determine the electrodes that measured an LFP measurement having a highest powered signal in a beta band (e.g., 8-33 Hertz (Hz)). For instance, the processing circuitry may determine which electrodes have the highest current source density (CSD), and the electrodes having the highest CSD may be electrodes that are most proximal to the signal source. The electrodes determined to be most proximal to the signal source are electrodes that are selected to deliver therapy. Selecting electrodes that are most proximal to the signal source is one example, and should not be considered limiting. In general, the processing circuitry may utilize the LFP measurements to determine which electrodes to use for stimulation in any of a variety of ways.

However, once the processing circuitry selects the electrodes to use for delivery of electrical stimulation, the clinician may need to expend a lengthy trial and error process to find the appropriate values for therapy parameters, such as amplitude, frequency, and pulse width, of the therapy to be delivered via the most proximal electrodes. This disclosure describes example techniques to automate the selection of therapy parameters for the therapeutic electrical stimulation based on evoking signals, and evaluating the evoked signals.

As described in more detail, in some examples, the processing circuitry may use different examples of the evoked signals to determine different therapy parameters. For example, the processing circuitry may cause stimulation generation circuitry to deliver a stimulation signal having a frequency less than a threshold frequency (e.g., less than 80 Hz), including outputting a single stimulation pulse, and sweep across a range of amplitudes and/or pulse widths to generate a plurality of evoked potential signals. For instance, the processing circuitry may cause the stimulation generation circuitry to deliver a first stimulation signal having frequency less than the threshold frequency at a first amplitude to generate a first evoked potential signal, deliver a second stimulation signal having frequency less than the threshold frequency at a second amplitude to generate a second evoked potential signal, and so forth. In some examples, the processing circuitry may determine at least one of an amplitude or pulse width for the therapeutic electrical stimulation signal based on the plurality of evoked potential signals.

The processing circuitry may cause stimulation generation circuitry to deliver a stimulation signal having a frequency greater than the threshold frequency (e.g., greater than 80 Hz), and sweep across a range of frequencies to generate a plurality of ERNA signals. For instance, the processing circuitry may cause the stimulation generation circuitry to deliver a first stimulation signal having frequency greater than the threshold frequency at a first frequency to generate a first ERNA signal, deliver a second stimulation signal having frequency greater than the threshold frequency at a second frequency to generate a second ERNA signal, and so forth. In some examples, the processing circuitry may determine a frequency for the therapeutic electrical stimulation signal based on the plurality of ERNA signals.

In the above examples, the processing circuitry may sweep across amplitude and/or pulse width of the stimulation signals having frequency less than threshold frequency to generate evoked potential signals to determine at least one of an amplitude or pulse width of the therapeutic electrical stimulation signal, and sweep across frequency of the stimulation signals having frequency greater than threshold frequency to generate ERNA signals to determine frequency of the therapeutic electrical stimulation signal. However, the example techniques are not so limited.

In some examples, the processing circuitry may sweep across amplitude and/or pulse width of the stimulation signals having frequency greater than threshold frequency to generate ERNA signals to determine at least one of an amplitude or pulse width of the therapeutic electrical stimulation signal, and sweep across frequency of the stimulation signals having frequency less than threshold frequency to generate evoked potential signals to determine frequency of the therapeutic electrical stimulation signal. In some examples, the processing circuitry may determine amplitude and/or pulse width and frequency of the therapeutic electrical stimulation signal using ERNA signals (e.g., sweeping amplitude and frequency of the stimulation signal used to generate ERNA signals), and not use evoked potential signals. In some examples, the processing circuitry may determine amplitude and/or pulse width and frequency of the therapeutic electrical stimulation signal using evoked potential signals (e.g., sweeping amplitude and frequency of the stimulation signal used to generate evoked potential signals), and not use ERNA signals. Also, in some examples, the processing circuitry may use evoked potential signals and/or ERNA signals to determine pulse width of the stimulation pulses, in addition to or instead of amplitude and frequency.

Accordingly, in techniques described in this disclosure, the processing circuitry may be configured to control stimulation generation circuitry to deliver a plurality of electrical stimulation signals. Although possible, the electrical stimulation signals need not necessarily provide therapeutic effect. However, in one or more examples, the electrical stimulation signals may each evoke a respective evoked signal (e.g., evoked potential signals or ERNA signals). For instance, the first electrical stimulation signal may evoke a first evoked signal, the second electrical stimulation may evoke a second evoked signal, and so forth.

Each of the electrical stimulation signals, used to evoke respective evoked signals, may have at least one parameter that is different. For instance, two or more of the electrical stimulation signals used to evoke evoked potential signals may have a different amplitude, pulse width, or frequency, and two or more of the electrical stimulation signals used to evoke ERNA signals may have a different amplitude, pulse width, or frequency, or vice-versa.

As an example, to generate evoked potential signals, the processing circuitry may control the stimulation generation circuitry to deliver N electrical stimulation signals. The frequency and pulse width of each of the N electrical stimulation signals may be the same, but the processing circuitry may change the amplitude of each of the N electrical stimulation signals. For example, the processing circuitry may sweep the amplitude from a minimum (e.g., 0.5 mA) to a maximum (e.g., 5 mA) at certain increments (e.g., 0.5 mA). For example, the processing circuitry may set the amplitude of the first electrical stimulation signal of the N electrical stimulation signals equal to 0.5 mA, set the amplitude of the second electrical stimulation signal of the N electrical stimulation signals equal to 1 mA, and so forth. Accordingly, in this example, for the N electrical stimulation signals, there may be N respective evoked potential signals. The above example describes sweeping the amplitude. In some examples, the processing circuitry may sweep pulse width from a minimum to a maximum at certain increments.

As an example, to generate ERNA signals, the processing circuitry may control the stimulation generation circuitry to deliver N electrical stimulation signals. The amplitude and pulse width of each of the N electrical stimulation signals may be the same, but the processing circuitry may change the frequency of each of the N electrical stimulation signals. For example, the processing circuitry may sweep the frequency from a minimum (e.g., 80 Hz) to a maximum (e.g., 220 Hz) in at certain increments (e.g., 5 Hz). For example, the processing circuitry may set the frequency of the first electrical stimulation signal of the N electrical stimulation signals equal to 80 Hz, set the frequency of the second electrical stimulation signal of the N electrical stimulation signals equal to 85 Hz, and so forth. Accordingly, in this example, for the N electrical stimulation signals, there may be N respective ERNA signals.

Again, although generating evoked potential signals is described by changing amplitude, and generating ERNA signals is described by changing frequency, the example techniques are not so limited. The processing circuitry may generate evoked potential signals by sweeping frequency (and/or pulse width), and generate ERNA signals by sweeping amplitude (and/or pulse width). Also, in some examples, the processing circuitry may utilize ERNA signals to determine at least one parameter for the therapeutic electrical stimulation signal, and not utilize evoked potential signals, or may utilize evoked potential signals to determine at least one parameter for the therapeutic electrical stimulation signal, and not utilize ERNA signals.

The processing circuitry may be configured to determine parameters for a therapeutic electrical stimulation signal based on the respective evoked signals. For example, the processing circuitry may evaluate the characteristics of the evoked signals to determine the parameters for the therapeutic electrical stimulation signal. As one example, the processing circuitry may be configured to determine one or more of peak-to-trough amplitude, time between peak-to-peak, change in peak amplitudes (e.g., damping rate), amount of oscillation (e.g., ringing of the respective ERNA signals), rise or fall times, or frequency shift from early resonance to late resonance of the respective ERNA signals, and possibly other characteristics of the respective evoked signals, such as features not characterized by a dampened oscillator (e.g., features that are not similar to a signal generated by a dampened oscillator).

Based on the respective characteristics of the evoked signals, the processing circuitry may select one of the evoked signals. For instance, the processing circuitry may select the ERNA signal having the greatest peak-to-trough amplitude, or select the ERNA signal having the most change in peak amplitudes (e.g., fastest damping rate). As another example, the processing circuitry may select the evoked potential signal having the greatest amplitude.

The processing circuitry may determine the parameters of the electrical stimulation signal that evoked the selected evoked signal, and use the determined parameters to determine at least one parameter for the therapeutic electrical stimulation signal. For instance, as an example, the processing circuitry may determine that the electrical stimulation signal, used to generate an evoked potential signal, having an amplitude of 1 mA evoked the selected evoked potential signal. The processing circuitry may set the amplitude parameter equal to 1 mA for the therapeutic electrical signal.

As another example, the processing circuitry may determine that the electrical stimulation signal having a frequency of 130 Hz evoked the selected ERNA signal (e.g., the ERNA signal having the greatest peak-to-trough amplitude). The processing circuitry may set the frequency parameter equal to 130 Hz for the therapeutic electrical stimulation signal.

The processing circuitry may select a particular evoked signal from the respective evoked signals based on various factors. For example, based on experimentation, it may be known that stimulation signals that provide therapeutic effect tend to also evoke evoked signals have specific characteristics. Accordingly, by evaluating the evoked signals to identify an evoked signal that tends to correlate with evoked signals generated from therapeutic electrical stimulation signals, the processing circuitry may be configured to determine the parameters for the therapeutic electrical stimulation signal.

By using the LFP measurements to identify the electrode (s) that should be used for stimulation, the example techniques may reduce the number of electrodes over which the respective evoked signals are evoked. For instance, if the LFP measurement is not used, then the processing circuitry may evoke N respective evoked signals for a first electrode, evoke N respective evoked signals for a second electrode, and so forth, which can result in a relatively large number of evoked signals that are evoked and evaluated. However, by using LFP measurements, the processing circuitry may narrow down the number of electrodes that are needed to deliver stimulation to evoke the respective evoked signals, the example techniques may reduce the amount of time and the processing power needed to determine the parameters for the therapeutic electrical stimulation signal.

There may be benefit in using evoked signals for determining the parameters for the therapeutic electrical stimulation signal, as compared to other signals such as LFP measurements. As one example, LFP measurements may be less reliable in cases of high ECG artifact. For instance, ECG signals may impact measurements of LFP more than evoked signals, such as ERNA signals. Accordingly, the LFP measurements may be well suited for determining which electrodes to use for stimulation (e.g., even in instances where there is ECG artifact), and ERNA signals may be well suited for determining parameters for the therapeutic electrical stimulation signals.

Although evoked signals may be useful for determining parameters for the therapeutic electrical stimulation signals, in some examples, the processing circuitry may determine whether to use evoked signals based on information from another sensor. As an example, output from an accelerometer may indicate the posture of the patient. The reliability of the evoked signals for determining parameters for the therapeutic electrical stimulation signals may be based on posture of the patient. In some examples, based on the posture information of the patient from the accelerometer, the processing circuitry may selectively determine whether to use the evoked signals for determining parameters for the therapeutic electrical stimulation signals.

In the above examples, LFP measurements are used for determining which electrodes to use for stimulation, and evoked signals are used for determining parameters for therapeutic electrical stimulation signals. In some examples, the processing circuitry may use evoked signals for determining which electrodes to use for stimulation, and for determining parameters for therapeutic electrical stimulation signals, such as when there is too much noise on the LFP measurements (e.g., due to excessive ECG artifacts). As another example, the processing circuitry may use input from another sensor (e.g., accelerometer) to determine reliability of the evoked signals or LFP measurements. Based on the reliability determination, the processing circuitry may use evoked signals or LFP measurements for determining which electrodes to use for stimulation, and possibly the parameters for therapeutic electrical stimulation signals.

FIG. 1 is a conceptual diagram illustrating an example system 100 that includes an implantable medical device (IMD) 106 configured to deliver deep brain stimulation (DBS) to a patient 112. In some examples, the DBS may be adaptive in the sense that IMD 106 may adjust, increase, or decrease the magnitude of one or more parameters of the DBS in response to changes in patient activity or movement, a severity of one or more symptoms of a disease of the patient, a presence of one or more side effects due to the DBS, or one or more sensed signals of the patient.

For instance, one example of system 100 is a bi-directional DBS system with capabilities to both deliver stimulation, sense intrinsic neuronal signals, and sense neural signals that are evoked in response to delivery of stimulation. System 100 may be configured to treat a patient condition, such as a movement disorder (e.g., essential tremor (ET) or Parkinson's), neurodegenerative impairment, a mood disorder, or a seizure disorder of patient 112. Patient 112 ordinarily is a human patient. In some cases, however, therapy system 100 may be applied to other mammalian or non-mammalian, non-human patients. While movement disorders and neurodegenerative impairment are primarily referred to herein, in other examples, therapy system 100 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post-traumatic stress disorder, dysthymic disorder, and obsessive-compulsive disorder (OCD)). At least some of these disorders may be manifested in one or more patient movement behaviors. As described herein, a movement disorder or other neurodegenerative impairment may include symptoms such as, for example, muscle control impairment, motion impairment or other movement problems, such as rigidity, spasticity, bradykinesia, rhythmic hyperkinesia, nonrhythmic hyperkinesia, and akinesia. In some cases, the movement disorder may be a symptom of Parkinson's disease or essential tremor (ET). However, the movement disorder may be attributable to other patient conditions.

Example therapy system 100 includes medical device programmer 104, implantable medical device (IMD) 106, lead extension 110, and leads 114A and 114B with respective sets of electrodes 116, 118. In the example shown in FIG. 1, electrodes 116, 118 of leads 114A, 114B are positioned to deliver electrical stimulation to a tissue site within brain 120, such as a deep brain site under the dura mater of brain 120 of patient 112. In some examples, delivery of stimulation to one or more regions of brain 120, such as the subthalamic nucleus (STN), globus pallidus or thalamus, ventralus intermediate (VIM), anterior nucleus (ANT), ventral internal capsule/ventral striatum (VCVS), cortico-basal ganglia-thalamocortical circuit, or anterior insular cortex (AIC), may be an effective treatment to manage disorders, such as Parkinson's disease. Some or all of electrodes 116, 118 also may be positioned to sense neurological brain signals within brain 120 of patient 112. In some examples, some of electrodes 116, 118 may be configured to sense neurological brain signals and others of electrodes 116, 118 may be configured to deliver electrical stimulation to brain 120. In other examples, all of electrodes 116, 118 are configured to both sense neurological brain signals and deliver electrical stimulation to brain 120. In some examples, unipolar stimulation may be possible where one electrode is on the housing of IMD 106.

IMD 106 includes a therapy module (e.g., which may include processing circuitry or other electrical circuitry configured to perform the functions attributed to IMD 106) that includes stimulation generation circuitry configured to generate and deliver electrical stimulation therapy to patient 112 via a subset of electrodes 116, 118 of leads 114A and 114B, respectively. The subset of electrodes 116, 118 that are used to deliver electrical stimulation to patient 112, and, in some cases, the polarity of the subset of electrodes 116, 118, may be referred to as a stimulation electrode combination. As described in further detail below, the stimulation electrode combination can be selected for a particular patient 112 and target tissue site (e.g., selected based on the patient condition). The group of electrodes 116, 118 includes at least one electrode and can include a plurality of electrodes. In some examples, the plurality of electrodes 116 and/or 118 may have a complex electrode geometry such that two or more electrodes are located at different positions around the perimeter of the respective lead.

In some examples, the neurological signals sensed within brain 120 may reflect changes in electrical current produced by the sum of electrical potential differences across brain tissue. There may be various examples of neurological brain signals that electrodes 116, 118 may be configured to sense. One example of a neurological brain signal is a local field potential (LFP). An LFP may be an intrinsic signal within brain 120 of patient 112 that is generated by a signal source within brain 120 of patient 112. Another example of a neurological brain signal is an evoked signal, such as an evoked potential signal or an evoked resonant neural activity (ERNA) signal. Delivery of electrical stimulation within brain 120 may evoke an evoked signal, and the evoked signal may not be an intrinsic signal. The electrical stimulation delivered within brain 120 to evoke the evoked signal need not necessarily provide therapeutic benefit, but therapeutic benefit from the electrical stimulation used to evoke the evoked signal is possible. Electroencephalogram (EEG) signal or an electrocorticogram (ECoG) signal are also examples of neurological signals. For example, neurons generate the neurological signals, and if measured at depth, it is LFP or evoked signal, if measured on the dura, it is ECoG, and if on scalp, it is EEG.

In some examples, the delivery of therapeutic electrical stimulation signals may be based on a feature of interest (e.g., biomarker). One example of the feature of interest (e.g., biomarker) within the LFPs is synchronized beta frequency band (8-33 Hz) LFP activity recorded within the sensorimotor region of the subthalamic nucleus (STN) in Parkinson's disease or essential tremor patients. The source of the LFP activity can be considered as a signal source, within the brain of the patient, that outputs an oscillatory electrical voltage signal that is sensed by one or more of electrodes 116 and/or 118. The suppression of pathological beta activity (e.g., suppression or squelching of the signal component of the bioelectric signals generated from the LFP source that is within the beta frequency band) by both medication and DBS may correlate with improvements in the motor symptoms of patients who have Parkinson's disease or essential tremor.

For example, one or more of electrodes 116 and/or 118 may sense the LFP activity. Accordingly, there may be a plurality of LFP measurements of an LFP. For instance, each of the LFP measurements are measured with different electrodes 116 and/or 118 on leads 114A, 114B. As described, the LFP is intrinsically generated by a signal source (e.g., oscillatory electrical voltage source) within brain 120 of patient 122.

In some examples, the neurological brain signals that are used to select a stimulation electrode combination may be sensed within the same region of brain 120 as the target tissue site for the electrical stimulation. As previously indicated, these tissue sites may include tissue sites within anatomical structures such as the thalamus, subthalamic nucleus or globus pallidus of brain 120, as well as other target tissue sites. The specific target tissue sites and/or regions within brain 120 may be selected based on the patient condition. Thus, in some examples, both a stimulation electrode combination and sense electrode combinations may be selected from the same set of electrodes 116, 118. In other examples, the electrodes used for delivering electrical stimulation may be different than the electrodes used for sensing neurological brain signals.

Therapeutic electrical stimulation generated by IMD 106 may be configured to manage a variety of disorders and conditions. In some examples, the stimulation generation circuitry of IMD 106 is configured to generate and deliver therapeutic electrical stimulation pulses to patient 112 via electrodes of a selected stimulation electrode combination. However, in other examples, the stimulation generation circuitry of IMD 106 may be configured to generate and deliver a continuous wave signal, e.g., a sine wave or triangle wave. In either case, stimulation generation circuitry within IMD 106 may generate the electrical stimulation therapy for DB S according to a selected therapy program. In examples in which IMD 106 delivers therapeutic electrical stimulation in the form of stimulation pulses, a therapy program may include a set of therapy parameter values (e.g., parameters), such as a stimulation electrode combination for delivering stimulation to patient 112, pulse frequency, pulse width, and a current or voltage amplitude of the pulses. As previously indicated, the electrode combination may indicate the specific electrodes 116, 118 that are selected to deliver therapeutic stimulation signals to tissue of patient 112 and the respective polarities of the selected electrodes.

Figure 5A:
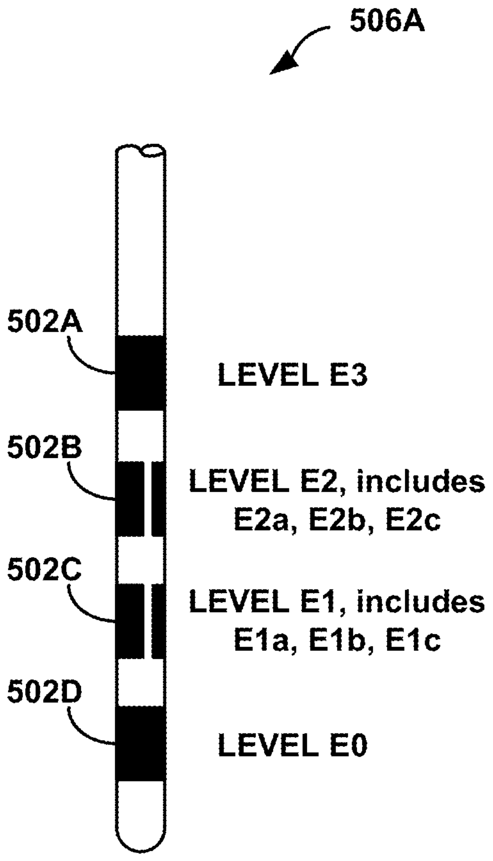
FIGS. 5A and 5B are conceptual diagrams illustrating examples of leads that configured to be implanted within a brain of a patient.
Figure 5B:
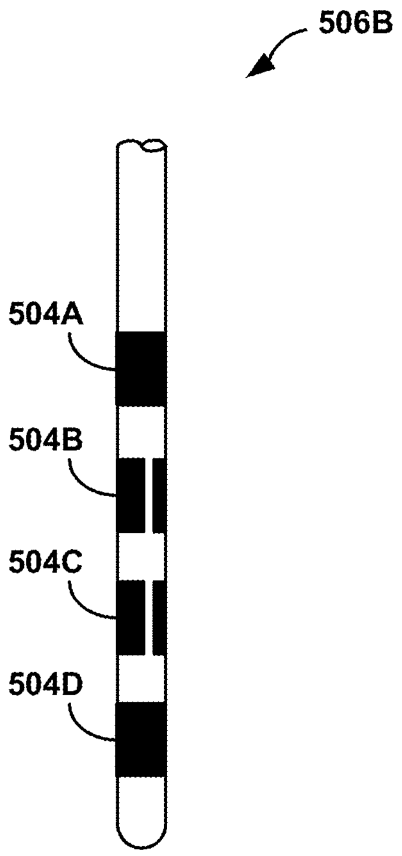

In some examples, electrodes 116, 118 may be circumferentially-segmented DBS arrays of electrodes, and include some non-segmented electrodes as well, such as ring electrodes. Circumferentially-segmented DBS arrays refer to electrodes that are segmented circumferentially along the lead. As one example, leads 114A and 114B may include a first set of electrodes arranged circumferentially around leads 114A and 114B that are all at the same height level on leads 114A and 114B. Each of the electrodes in the first set of electrodes is a separate segmented electrode and form a level of circumferentially-segmented array of electrodes. Leads 114A and 114B may include a second set of electrodes arranged circumferentially around leads 114A and 114B that are all at the same height level on leads 114A and 114B. Each of the electrodes in the first set of electrodes is a separate segmented electrode and form a level of circumferentially-segmented array of electrodes. The electrodes may be beneficial by enabling directional stimulation and sensing. An example of such electrodes is illustrated in FIGS. 5A and 5B.

With the electrodes, IMD 106 may be configured to perform both directional stimulation and sensing, thereby enhancing the ability to target the source of the LFP activities (also referred to as pathological neuronal activities). For example, IMD 106 may be configured to perform directional sensing to determine a direction and/or orientation of the LFP source (e.g., signal source that generates the LFP) having the signal component in the beta frequency band. IMD 106 may direct the electrical stimulation toward the signal source to suppress (e.g., squelch) the signal component produced by the signal source in the beta frequency band, as one example. This disclosure describes example techniques to utilize ERNA signals to determine the parameters of the therapeutic electrical stimulation signals used to suppress the signal component produced by the signal source in the beta frequency band.

The signal component in the beta frequency band is described as one example, and the techniques are applicable to other types of LFP activity. Furthermore, the example techniques are not limited to examples where one or more of electrodes 116, 118 are circumferentially-segmented electrodes. The example of using circumferentially-segmented electrodes is described as a way of directional stimulation and sensing. However, the example techniques are also useable in examples where directional stimulation and sensing are not available or are not used. Moreover, there may be other ways of performing directional stimulation and sensing that do not require the use of circumferentially-segmented electrodes.

To suppress the signal component having the beta frequency band from the LFP source (e.g., the signal source of the LFP), IMD 106 may output an electrical stimulation signal that alters the way in which neurons of the LFP source produce signals. For example, the electrical stimulation either directly inhibits a certain neuronal population that includes the LFP source or excites one group of neurons which in turn suppresses another group of neurons (e.g., network effect). The stimulation may act on the neurons directly, and not necessarily on the signals the neurons (e.g., LFP source) produces.

To suppress the signal component having the beta frequency band from the signal source of the LFP may include at least two parts. The first part is to determine which electrodes 116, 118 to use to deliver the therapeutic electrical stimulation signal. The second part is to determine the parameters of the therapeutic electrical stimulation signal such as amplitude, frequency, and pulse width of the therapeutic electrical stimulation signal. The example techniques described in this disclosure may utilize at least two different neurological signals to determine which electrodes 116, 118 to use to deliver the therapeutic electrical stimulation, and the parameters of the therapeutic electrical stimulation signal.

For example, the processing circuitry of IMD 106 may be configured to determine a plurality of LFP measurements of an LFP. In some examples, each of the LFP measurements are measured with different electrodes 116, 118 on leads 114A, 114B. As one example, one of electrodes 118 may be a reference electrode (e.g., ground), and the processing circuitry may receive a first LFP measurement that is sensed by a first one of electrodes 116 relative to the reference electrode of electrodes 118. The processing circuitry may receive a second LFP measurement that is sensed by a second one of electrodes 116 relative to the reference electrode of electrodes 118, and so forth.

Although the above examples describes the reference electrode being one of electrodes 118, and receiving the LFP measurements through electrodes 116, the techniques are not so limited. In some examples, the reference electrode may be one of electrodes 116, and the processing circuitry may receive the LFP measurements through electrodes 118. In some examples, the reference electrode need not be one of electrodes 116 or 118, and may be another electrode, such as an electrode on the housing of IMD 106.

Examples where the reference electrode is on one of leads 114A or 114B, and the other electrode used for sensing the LFP (e.g., determining the LFP measurement) is on the other of leads 114A or 114B or on the housing of IMD 106 is referred to as a monopolar sensing. In some examples, to determine the plurality of LFP measurements, the processing circuitry may receive bipolar sensing measurements. In bipolar sensing measurements, electrodes 116, 118 for sensing are on the same one of leads 114A, 114B.

For ease of description, this disclosure describes monopolar sensing, but the example techniques are applicable to bipolar sensing as well. Also, for ease of description, for monopolar sensing, the example techniques are described with respect to the reference electrode being one of electrodes 118, and other electrode used for sensing being one of electrodes 116. Accordingly, the processing circuitry may determine a plurality of LFP measurements of an LFP. In some examples, each of the LFP measurements is measured with different electrodes 116 on lead 114A.

The processing circuitry of IMD 106 may be configured to determine one or more electrodes 116 on lead 114A for delivering therapeutic electrical stimulation signal based on the LFP measurements. As one example, processing circuitry of IMD 106 may determine which LFP measurement had the highest powered beta band signal (e.g., signal in 8-33 Hz of the LFP measurement) of electrodes 116, and may determine that the one of electrodes 116 having the LFP measurement with highest powered beta band signal is the electrode of electrodes 116 to use for delivery of therapeutic electrical stimulation signal. The return electrode for the therapeutic stimulation signal may be an electrode on the housing of IMD 106 or may be one of electrodes 116, 118.

There may be various ways in which to determine the LFP measurement having the highest powered beta band signal. In some examples, the LFP measurements are time-varying, and can possibly be sinusoidal.

This disclosure describes using current source density (CSD) as a way in which to determine the highest powered beta band signal, but the example techniques should not be considered limited to using CSD for determining the highest powered beta band signal. For example, the processing circuitry may bandpass filter the LFP measurement so that the frequency components in the beta band remain (e.g., filter out frequency components that are not in beta band). Instead of or in addition to CSD, the processing circuitry of IMD 106 may determine root-mean-square (RMS) value of the LFP measurements, and determine the LFP measurement having the largest RMS value. As another example, electrodes 116 may be coupled to a full-bridge or half-bridge rectifier. The processing circuitry may receive rectified LFP measurements, and determine an average of the rectified LFP measurements. The processing circuitry may determine the rectified LFP measurement having the highest average value. As another example, the processing circuitry may determine the maximum amplitude of the LFP measurements.

As another examples, in addition to or instead of CSD, the processing circuitry may utilize power spectral density (PSD). In PSD, the processing circuitry may determine a transform (e.g., Fourier transform, such as a fast Fourier transform (FFT)) to convert the LFP measurements into a frequency domain, and determine the power spectral density. The processing circuitry may remove the lowest power spectral density for normalization. The processing circuitry may determine the power spectral density in the beta band as one example way to determine the LFP measurements.

Also, the use of beta band is described as an example, and should not be considered limiting. In some examples, the processing circuitry may determine the LFP measurement having the highest power overall, and not just at the beta band. In some examples, the processing circuitry may determine the LFP measurement having the highest power at a frequency band other than the beta band. For example, the processing circuitry may determine the LFP measurement having the highest power in the 4-8 Hz band (e.g., theta band) or the 35-100 Hz band (e.g., gamma band).

Determining the LFP measurement with the highest CSD or any of the other example values described above may correlate with one or more electrodes 116 that are most proximal to the signal source that generates the LFP. That is, the electrode of electrodes 116 that is most proximal to the signal source that generates the LFP may also be the electrode of electrodes 116 having the highest CSD for the LFP measurement. In general, the electrodes of electrodes 116 and 118 that are most proximal to the LFP source tend to be the electrodes with which electrical stimulation should be delivered. Electrodes of electrodes 116 and 118 that are most proximal to the LFP source may be the electrodes having the highest current source density (CSD). For instance, electrodes of electrodes 116 and 118 that have the highest CSD are also the closest to the LFP source. However, the example techniques do not require selecting electrodes 116 or 118 that are most proximal to the signal source.

In this way, the processing circuitry of IMD 106 may determine one or more electrodes 116 on lead 104A for delivering therapeutic electrical stimulation signal based on the LFP measurements. The processing circuitry of IMD 106 may also determine the parameters for the therapeutic electrical stimulation signal. One example way to determine the parameters for the therapeutic electrical stimulation signal is based on evoked signals (e.g., evoked potential signals and/or ERNA signals).

For instance, the processing circuitry of IMD 106 may control the stimulation generation circuitry of IMD 106 to deliver a plurality of electrical stimulation signals via the determined one or more electrodes 116. In one or more examples, the plurality of electrical stimulation signals each include at least one different therapy parameter. For respective ones of the plurality of electrical stimulation signals, the processing circuitry of IMD 106 may determine respective evoked signals, where the respective evoked signals are evoked by delivery of the respective plurality of electrical stimulation signals. The processing circuitry may determine parameters for the therapeutic electrical stimulation signal based on the respective evoked signals.

As one example, to determine an amplitude parameter for the therapeutic electrical stimulation signal, two or more of the plurality of electrical stimulation signals have different amplitudes. The processing circuitry may determine respective evoked signals generated from plurality of electrical stimulation signals having different amplitudes, and determine the amplitude parameter for the therapeutic electrical stimulation signal. In some examples, the evoked signals that are used for determining the amplitude may be evoked potential signals (e.g., evoked potential signals generated with electrical stimulation signals having a frequency less than a threshold frequency). However, the example techniques are not so limited, and ERNA signals may be used.

As another example, to determine a frequency parameter for the therapeutic electrical stimulation signal, two or more of the plurality of electrical stimulation signals have different frequencies. The processing circuitry may determine respective evoked signals generated from plurality of electrical stimulation signals having different frequencies, and determine the frequency parameter for the therapeutic electrical stimulation signal. In some examples, the evoked signals that are used for determining the frequency may be ERNA signals (e.g., ERNA signals generated with electrical stimulation signals having a frequency higher than a threshold frequency). However, the example techniques are not so limited, and evoked potential signals may be used.

In some examples, the processing circuitry may use both evoked potential signals and ERNA signals to determine parameters for the therapeutic electrical stimulation signal. For example, the processing circuitry may keep frequency and pulse width of a plurality of electrical stimulation signals constant, and sweep across amplitudes to generate evoked signals (e.g., evoked potential signals). Based on the evoked signals, the processing circuitry may determine the amplitude for the therapeutic electrical stimulation signal. The processing circuitry may then keep amplitude and pulse width of a plurality of electrical stimulation signals constant, and sweep across frequencies to generate evoked signals (e.g., ERNA signals). Based on the evoked signals, the processing circuitry may determine the frequency for the therapeutic electrical stimulation signal.

In the above example, evoked potential signals (e.g., evoked signals generated with stimulation signals having frequency below a threshold frequency) are used to determine amplitude, and ERNA signals (e.g., evoked signals generated with stimulation signals having frequency above the threshold frequency) are used to determine frequency. However, the vice-versa may be possible, and evoked potential signals may be used to determine frequency, and ERNA signals may be used to determine amplitude. In some examples, only one of the evoked potential signals or ERNA signals may be used to determine amplitude and frequency.

Moreover, the examples are described with sweeping amplitude and/or frequency, while keeping pulse width constant. However, in some examples, the processing circuitry may also sweep across pulse widths over a range of pulse widths, while keeping amplitude and frequency constant, and use the evoked signals (e.g., evoked potential signals or ERNA signals) to determine the pulse width for the therapeutic electrical stimulation signal.

In this disclosure, the phrase "therapeutic electrical stimulation signal" is used to refer to electrical stimulation signal that is delivered for providing therapy. Delivery of the therapeutic electrical stimulation signal may evoke an evoked signal, but the techniques do not require the therapeutic electrical stimulation signal to evoke an evoked signal. The phrase "electrical stimulation signal" is used to refer to electrical stimulation signal that is delivered for evoking an evoked signal. Delivery of an electrical stimulation signal for evoking an evoked signal may provide therapeutic effect, but the techniques do not require the electrical stimulation signal used for evoking an evoked signal to provide therapeutic effect.

As described above, the processing circuitry may control stimulation generation circuitry to deliver a plurality of electrical stimulation signals via the determined one or more electrodes, where the plurality of electrical stimulation signals each include at least one different therapy parameter. For instance, the processing circuitry may control the stimulation generation circuitry to sweep across a range of frequencies such that frequency of each of the electrical stimulation signals is different (e.g., for ERNA signals), or sweep across a range of amplitudes or pulse widths such that amplitude and/or pulse width of each of the electrical stimulation signals is different (e.g., for evoked potential signals). That is, the processing circuitry may be configured to control the stimulation generation circuitry to deliver the plurality of electrical stimulation signals via the determined one or more electrodes, where a frequency for each of the plurality of electrical stimulation signals is within a range of frequencies (e.g., 80 Hz to 220 Hz). As another example, the processing circuitry may control the stimulation generation circuitry to sweep across a range of amplitudes and/or pulse widths such that the amplitude and/or pulse width of each of the electrical stimulation signals is different. That is, the processing circuitry may be configured to control the stimulation generation circuitry to deliver the plurality of electrical stimulation signals via the determined one or more electrodes, where an amplitude and/or pulse width for each of the plurality of electrical stimulation signals is within a range of amplitudes and/or pulse widths.

In accordance with one or more examples, for respective ones (e.g., for each) of the plurality of electrical stimulation signals, the processing circuitry may determine respective evoked signals, where the respective evoked signals are evoked by delivery of the respective plurality of electrical stimulation signals. For instance, the processing circuitry may determine a first evoked signal that is evoked by a first electrical stimulation signal, determine a second evoked signal that is evoked by a second electrical stimulation signal, and so forth.

The processing circuitry may evaluate the respective evoked signals for determining the parameters for the therapeutic electrical stimulation signal. For instance, the processing circuitry may determine characteristics of the respective evoked signals such as resonant activity for ERNA signals or peak amplitude for evoked potential signals. Examples of resonant activity include one or more of peak-to-trough amplitude, time between peak-to-peak, change in peak amplitudes (e.g., damping), amount of oscillations (e.g., number of peaks), rise or fall times, and frequency shift from early resonance to late resonance of the respective ERNA signals.

Based on the determined resonant activity or peak amplitude, the processing circuitry may select one of the ERNA signals and/or evoked potential signals. As an example, the processing circuitry may select the ERNA signal of the respective ERNA signals having the highest peak-to-trough amplitude. As another example, the processing circuitry may select the ERNA signal of the respective ERNA signals having the most of amount of oscillations (e.g., the most number of peaks before the ERNA signals dampens to noise level). As another example, the processing circuitry may select the ERNA signal of the respective ERNA signals having the fastest reduction in peak amplitudes (e.g., fastest damping). As another example, the processing circuitry may select the evoked potential signal of the respective evoked potential signals having the highest amplitude. The above provide a few non-limiting examples that the processing circuitry may evaluate to select an evoked signal, and other examples of are possible. Also, the processing circuitry may select an evoked signal based on a combination of factors (e.g., a weighting of two or more factors).

The processing circuitry may determine the respective electrical stimulation signal of the selected evoked signal, and may determine the parameters of the determined respective electrical stimulation signal. The processing circuitry may determine at least one parameter for the therapeutic electrical stimulation signal based on the determined parameters. In this way, the processing circuitry may determine parameters for the therapeutic electrical stimulation signal based on the respective evoked signals.

For instance, assume that the processing circuitry selected the third ERNA signal based on the resonant activity of the third ERNA signal. In this example, the processing circuitry may determine that the third electrical stimulation signal is the respective electrical stimulation signal that evoked the third ERNA signal. The processing circuitry may determine the parameters such as one or more of pulse width, amplitude, and frequency of the third electrical stimulation signal. The processing circuitry may determine the parameters of the therapeutic electrical stimulation signal based on the determined parameters of the third electrical stimulation signal. For instance, if the frequency of the third electrical stimulation signal was 130 Hz, the processing circuitry may determine the frequency of the therapeutic electrical stimulation signal to be 130 Hz.

As another example, assume that the processing circuitry selected the fifth evoked potential signal based on the fifth evoked potential signal having the largest amplitude. In this example, the processing circuitry may determine that the fifth electrical stimulation signal is the respective electrical stimulation signal that evoked the fifth evoked potential signal. The processing circuitry may determine the parameters such as one or more of pulse width, amplitude, and frequency of the fifth electrical stimulation signal. The processing circuitry may determine the parameters of the therapeutic electrical stimulation signal based on the determined parameters of the fifth electrical stimulation signal. For instance, if the amplitude of the fifth electrical stimulation signal was 1.5 mA, the processing circuitry may determine the amplitude of the therapeutic electrical stimulation signal to be 1.5 mA.

IMD 106 may be implanted within a subcutaneous pocket above the clavicle, or, alternatively, on or within cranium 122 or at any other suitable site within patient 112. Generally, IMD 106 is constructed of a biocompatible material that resists corrosion and degradation from bodily fluids. IMD 106 may comprise a hermetic housing to substantially enclose components, such as a processor, therapy module, and memory.

As shown in FIG. 1, implanted lead extension 110 is coupled to IMD 106 via connector 108 (also referred to as a connector block or a header of IMD 106). In the example of FIG. 1, lead extension 110 traverses from the implant site of IMD 106 and along the neck of patient 112 to cranium 122 of patient 112 to access brain 120. In the example shown in FIG. 1, leads 114A and 114B (collectively "leads 114") are implanted within the right and left hemispheres (or in just one hemisphere in some examples), respectively, of patient 112 in order to deliver electrical stimulation to one or more regions of brain 120, which may be selected based on the patient condition or disorder controlled by therapy system 100. The specific target tissue site and the stimulation electrodes used to deliver stimulation to the target tissue site, however, may be selected, e.g., according to the identified patient behaviors and/or other sensed patient parameters. For example, the target tissue site may be the location of the signal source that generates the LFP having a signal component in the beta frequency band. The stimulation electrodes used to deliver stimulation to the target tissue site may be those that are most proximal to the signal source, e.g., as determined by the electrodes having the highest CSD, RMS, peak value, rectified average value, etc. Other lead 114 and IMD 106 implant sites are contemplated. For example, IMD 106 may be implanted on or within cranium 122, in some examples. Leads 114A and 114B may be implanted within the same hemisphere or IMD 106 may be coupled to a single lead implanted in a single hemisphere, in some examples.

Existing lead sets include axial leads carrying ring electrodes disposed at different axial positions and so-called "paddle" leads carrying planar arrays of electrodes. In some examples, more complex lead array geometries may be used.

Although leads 114 are shown in FIG. 1 as being coupled to a common lead extension 110, in other examples, leads 114 may be coupled to IMD 106 via separate lead extensions or directly to connector 108. Leads 114 may be positioned to deliver electrical stimulation to one or more target tissue sites within brain 120 to manage patient symptoms associated with a movement disorder of patient 112. Leads 114 may be implanted to position electrodes 116, 118 at desired locations of brain 120 through respective holes in cranium 122. Leads 114 may be placed at any location within brain 120 such that electrodes 116, 118 are capable of providing electrical stimulation to target tissue sites within brain 120 during treatment. For example, electrodes 116, 118 may be surgically implanted under the dura mater of brain 120 or within the cerebral cortex of brain 120 via a burr hole in cranium 122 of patient 112, and electrically coupled to IMD 106 via one or more leads 114.

In the example shown in FIG. 1, electrodes 116, 118 of leads 114 are shown as ring electrodes. Ring electrodes may be used in DBS applications because ring electrodes are relatively simple to program and are capable of delivering an electrical field to any tissue adjacent to electrodes 116, 118. In other examples, electrodes 116, 118 may have different configurations. For example, at least some of the electrodes 116, 118 of leads 114 may have a complex electrode array geometry that is capable of producing shaped electrical fields. The complex electrode array geometry may include multiple electrodes (e.g., partial ring or segmented electrodes) around the outer perimeter of each lead 114, rather than one ring electrode. In this manner, electrical stimulation may be directed in a specific direction from leads 114 to enhance therapy efficacy and reduce possible adverse side effects from stimulating a large volume of tissue. For example, one or more electrodes 116, 118 may be circumferentially-segmented DBS arrays of electrodes, and one or more electrodes 116, 118 may be non-segmented electrodes such as ring electrodes, as described above, and as illustrated in FIGS. 5A and 5B. In some examples, electrodes 116, 118 may only be circumferentially-segmented DBS arrays of electrodes, and in some examples, electrodes 116, 118 may only be non-segmented electrodes, such as ring electrodes.

In some examples, a housing of IMD 106 may include one or more stimulation and/or sensing electrodes. In some examples, leads 114 may have shapes other than elongated cylinders as shown in FIG. 1. For example, leads 114 may be paddle leads, spherical leads, bendable leads, or any other type of shape effective in treating patient 112 and/or minimizing invasiveness of leads 114.

IMD 106 includes a memory to store a plurality of therapy programs that each define a set of therapy parameter values. In some examples, IMD 106 may select a therapy program from the memory based on various parameters, such as sensed patient parameters and the identified patient behaviors. For example, as described above, the processing circuitry of IMD 106 may determine parameters for the therapeutic electrical stimulation signal based on the respective evoked signals. In some examples, IMD 106 may output information indicative of the determined at least one parameter for clinician approval. After approval, the processing circuitry of IMD 106 may be store in a therapy program the determined parameter and may be configured to control stimulation generation circuitry of IMD 106 to deliver the therapeutic electrical stimulation signal based on the determined at least one parameter (e.g., by the processing circuitry selecting the therapy program that includes the determined parameters).

In some examples, clinician approval may not be necessary, such as in examples where the determined at least one parameter for the therapeutic electrical stimulation signal are within a "safe-range" as assigned by the surgeon/clinician. In such examples, the processing circuitry of IMD 106 may output information indicative of the determined at least one parameter for storage as a therapy program, and the stimulation generation circuitry may deliver the therapeutic electrical stimulation signal based on the determined at least one parameter (e.g., by processing circuitry selecting the therapy program that includes the determined at least one parameter). In this way, IMD 106 may generate therapeutic electrical stimulation based on the parameters of the selected therapy program to manage the patient symptoms associated with the patient disorder.

Rather than or in addition to using therapy programs, in some examples, it may be possible for the processing circuitry to directly output the information indicative of the determined at least one parameter to the stimulation generation circuitry. Accordingly, there may be various way in which the processing circuitry may output information indicative of the determined at least one parameter, such as to an external device like external programmer 104, described, below, to a therapy program, or to the stimulation generation circuitry.

External programmer 104 wirelessly communicates with IMD 106 as needed to provide or retrieve therapy information. Programmer 104 is an external computing device that the user, e.g., a clinician and/or patient 112, may use to communicate with IMD 106. For example, programmer 104 may be a clinician programmer that the clinician uses to communicate with IMD 106 and program one or more therapy programs for IMD 106. Alternatively, programmer 104 may be a patient programmer that allows patient 112 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 106.

When programmer 104 is configured for use by the clinician, programmer 104 may be used to transmit initial programming information to IMD 106. This initial information may include hardware information, such as the type of leads 114 and the electrode arrangement, the position of leads 114 within brain 120, the configuration of electrode array 116, 118, initial programs defining therapy parameter values, and any other information the clinician desires to program into IMD 106. Programmer 104 may also be capable of completing functional tests (e.g., measuring the impedance of electrodes 116, 118 of leads 114).

The clinician may also store therapy programs within IMD 106 with the aid of programmer 104. During a programming session, the clinician may determine one or more therapy programs that may provide efficacious therapy to patient 112 to address symptoms associated with the patient condition, and, in some cases, specific to one or more different patient states, such as a sleep state, movement state or rest state. For example, the clinician may select one or more stimulation electrode combinations with which stimulation is delivered to brain 120. During the programming session, the clinician may evaluate the efficacy of the specific program being evaluated based on feedback provided by patient 112 or based on one or more physiological parameters of patient 112 (e.g., muscle activity, muscle tone, rigidity, tremor, etc.). In some examples, evoked signals may be used to evaluate the efficacy of the specific program being evaluated (e.g., certain resonant activity in the ERNA signal may be indicative of efficacious therapy). Alternatively, identified patient behavior from video information may be used as feedback during the initial and subsequent programming sessions. Programmer 104 may assist the clinician in the creation/identification of therapy programs by providing a methodical system for identifying potentially beneficial therapy parameter values.

Programmer 104 may also be configured for use by patient 112. When configured as a patient programmer, programmer 104 may have limited functionality (compared to a clinician programmer) in order to prevent patient 112 from altering critical functions of IMD 106 or applications that may be detrimental to patient 112. In this manner, programmer 104 may only allow patient 112 to adjust values for certain therapy parameters or set an available range of values for a particular therapy parameter.

Programmer 104 may also provide an indication to patient 112 when therapy is being delivered, when patient input has triggered a change in therapy or when the power source within programmer 104 or IMD 106 needs to be replaced or recharged. For example, programmer 104 may include an alert LED, may flash a message to patient 112 via a programmer display, generate an audible sound or somatosensory cue to confirm patient input was received, e.g., to indicate a patient state or to manually modify a therapy parameter.

The above examples for determining one or more electrodes 116 on lead 114A for delivering therapeutic electrical stimulation signal based on the LFP measurements and for determining parameters for the therapeutic electrical stimulation were described with respect to the processing circuitry of IMD 106. In some examples, the processing circuitry of external programmer 104 may perform various techniques described above with respect to the processing circuitry of IMD 106. For instance, the processing circuitry of programmer 104 may determine one or more electrodes on lead 116 for delivering therapeutic electrical stimulation signals, and determine parameters for the therapeutic electrical stimulation signal based on the respective ERNA signals. As an example, IMD 106 may output the plurality of LFP measurements of an LFP to the processing circuitry of programmer 104 for determining one or more electrodes 116 on lead 114A for delivering therapeutic electrical stimulation signal based on the LFP measurements. As another example, IMD 106 may output the determined respective evoked signals (e.g., evoked potential signals and/or ERNA signals), where the respective evoked signals are evoked by delivery of the respective plurality of electrical stimulation signals to the processing circuitry of programmer 104, and the processing circuitry of programmer 104 may determine at least one parameter (e.g., determine parameters) for the therapeutic electrical stimulation signal based on the respective evoked signals.

Moreover, in some examples, the example techniques may be performed in the "cloud." For example, IMD 106 and/or programmer 104 may upload the LFP measurements and evoked signals to one or more servers that form a cloud computing environment. Processing circuitry of the cloud computing environment may determine the one or more electrodes 116 for delivering therapeutic electrical stimulation signal based on the LFP measurements, and/or determine parameters for the therapeutic electrical stimulation signal based on the respective evoked signals. Accordingly, in this disclosure, the processing circuitry that is configured to perform the example techniques may be any one or combination of the processing circuitry of IMD 106, the processing circuitry of programmer 104, and/or processing circuitry of a cloud computing environment.

Therapy system 100 may be implemented to provide chronic stimulation therapy to patient 112 over the course of several months or years. However, system 100 may also be employed on a trial basis to evaluate therapy before committing to full implantation. If implemented temporarily, some components of system 100 may not be implanted within patient 112. For example, patient 112 may be fitted with an external medical device, such as a trial stimulator, rather than IMD 106. The external medical device may be coupled to percutaneous leads or to implanted leads via a percutaneous extension. If the trial stimulator indicates DBS system 100 provides effective treatment to patient 112, the clinician may implant a chronic stimulator within patient 112 for relatively long-term treatment.

Although IMD 106 is described as delivering electrical stimulation therapy to brain 120, IMD 106 may be configured to direct electrical stimulation to other anatomical regions of patient 112. Further, an IMD may provide other electrical stimulation such as spinal cord stimulation to treat a movement disorder.

As described above, one example way to determine one or more electrodes on the lead for delivering therapeutic electrical stimulation signal based on the LFP measurements is to determine CSD of the one or more electrodes. The following provides an example of determining CSD. As noted above, using CSD for determining which electrodes 116 are used for delivering therapeutic electrical stimulation signal is one example, and should not be considered limiting.

IMD 106 may receive a plurality of LFP measurements generated by the signal source via electrodes 116, 118. The plurality of LFP measurements may be multiple voltage measurements of the LFP. IMD 106 may band pass filter the multiple LFP measurements to generate a plurality of filtered signals, where each filtered signal is from each of electrodes 116, 118. For instance, IMD 106 may generate a first filtered signal from the output of a first one of electrodes 116 that sensed the LFP, generate a second filtered signal for a second one of electrodes 116, and so forth.

From each of the filtered signals, IMD 106 may determine a current source density (CSD) value for each respective electrodes 116, 118. For example, the CSD values may be computed using all the signals from all the electrodes 116, 118. A single CSD value for a given electrode may need the signals sensed by that electrode and from adjacent electrodes. The CSD value of an electrode is a measure of the net current flow across an electrode. IMD 106 may determine which ones of electrodes 116, 118 have the highest CSD value. The electrodes 116, 118 having the highest CSD values tend to be electrodes most proximal to the signal source, and also tend to be the electrodes (or neighbor electrodes) that should be used to deliver the therapeutic electrical stimulation signal. Hence, the CSD value may be used to infer proximity of an electrode to a signal source that generates the LFP.

One example way to determine the CSD for respective electrodes is based on voltage differences of adjacent electrodes. For example, IMD 106 may determine CSD values based on the voltage differences between the adjacent electrodes. In some examples, the CSD values may be the second spatial difference of voltage difference along the electrodes. Each of the second spatial difference of voltage differences may be a difference between the voltage differences. In other words, in some examples, the CSD values may be the differences between the voltage differences along the lead. In a more specific example, the two CSD values for a four-electrode system would be $(V_1-V_2)-(V_2-V_3)$ and $(V_2-V_3)-(V_3-V_4)$.

IMD 106 may determine a CSD value for each electrode that is between two other electrodes. In general, in systems that include N electrodes, IMD 106 may determine N-2 CSD values, each of which may be associated with a different one of the electrodes. The end electrodes (e.g., the electrodes not arranged between two adjacent electrodes) may not have associated CSD values in some examples because the outside electrodes may not be associated with two different voltage difference values.

Figure 2:
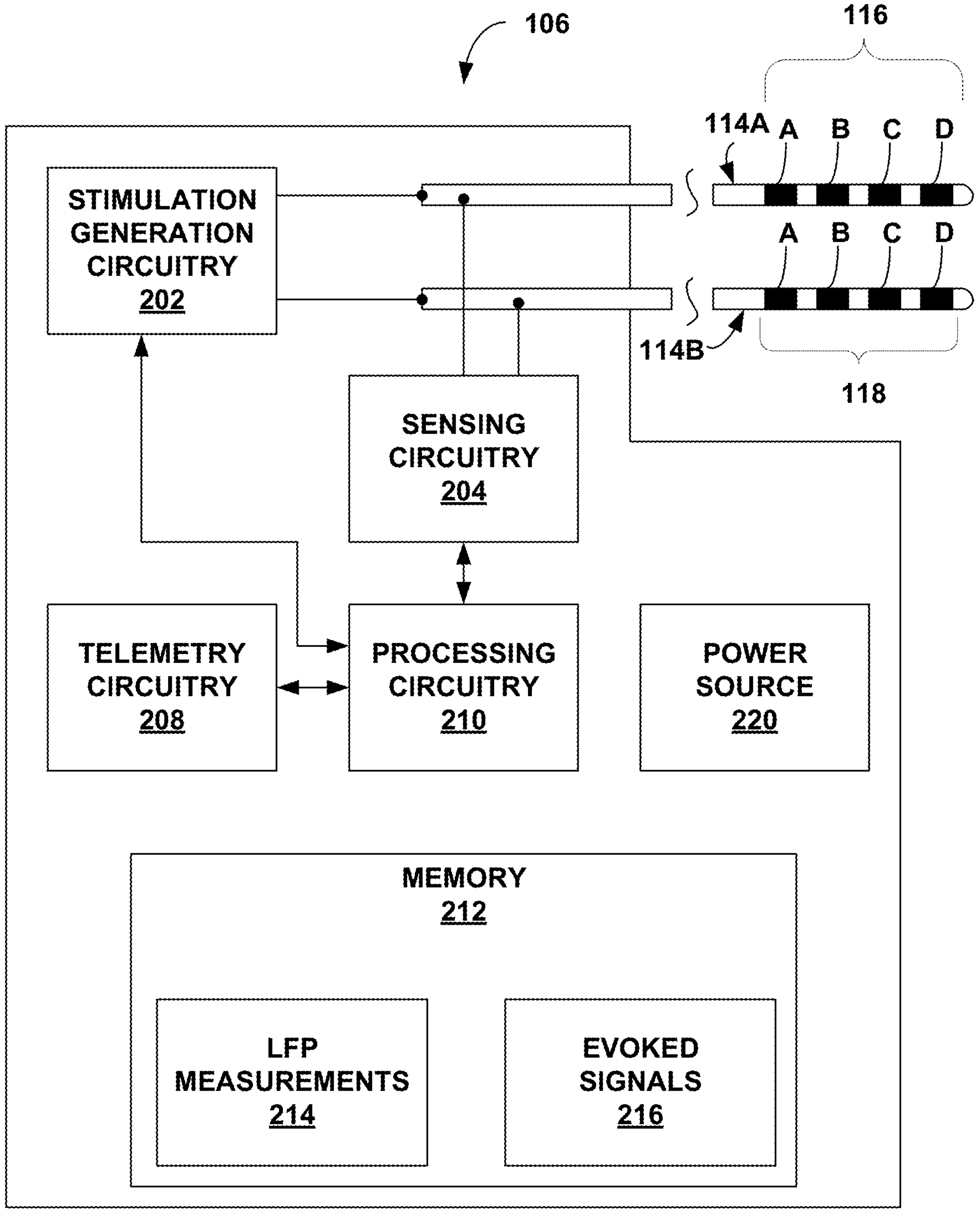
FIG. 2 is a block diagram of the example IMD of FIG. 1 for delivering DBS therapy according to an example of the techniques of the disclosure.

FIG. 2 is a block diagram of the example IMD 106 of FIG. 1 for delivering deep brain stimulation therapy. In the example shown in FIG. 2, IMD 106 includes processing circuitry 210, memory 212, stimulation generation circuitry 202, sensing circuitry 204, switch circuitry 206, telemetry circuitry 208, and power source 220. Each of these circuits may be or include electrical circuitry configured to perform the functions attributed to each respective circuit. Memory 212 may include any volatile or non-volatile media, such as a random-access memory (RAM), read only memory (ROM), non-volatile RAM (NVRAM), electrically erasable programmable ROM (EEPROM), flash memory, and the like. Memory 212 may store computer-readable instructions that, when executed by processing circuitry 210, cause IMD 106 to perform various functions. Memory 212 may be a storage device or other non-transitory medium.

In the example shown in FIG. 2, memory 212 stores LFP measurements 214 and evoked signals 216. LFP measurements 214 may be the plurality of local field potential LFP measurements of an LFP that processing circuitry 210 receives. For instance, each of the LFP measurements is measured with different electrodes 116, 118 on a lead 114A, 114B. As described, the LFP is intrinsically generated by a signal source within brain 120 of patient 122. Evoked signals 216 may be information indicative of the evoked potential signals and/or ERNA signals that are evoked by delivery of the respective plurality of stimulation signals that IMD 106 delivers for evoking the respective evoked signals.

Stimulation generation circuitry 202, under the control of processing circuitry 210, generates stimulation signals (e.g., electrical stimulation signals for evoking evoked signals and/or therapeutic electrical stimulation signals for delivering therapy) for delivery to patient 112 via selected combinations of electrodes 116, 118. An example range of electrical parameters believed to be effective in DBS to manage a movement disorder of patient include:

1. Pulse Rate, i.e., Frequency: between approximately 40 Hertz and approximately 500 Hertz, such as between approximately 100 to 220 Hertz or such as approximately 130 Hertz.
2. In the case of a voltage controlled system, Voltage Amplitude: between approximately 0.1 volts and approximately 50 volts, such as between approximately 2 volts and approximately 3 volts.
3. In the case of a current controlled system, Current Amplitude: between approximately 1 milliamps to approximately 3.5 milliamps, such as between approximately 1.0 milliamps and approximately 1.75 milliamps.
4. Pulse Width: between approximately 50 microseconds and approximately 500 microseconds, such as between approximately 50 microseconds and approximately 200 microseconds.

Accordingly, in some examples, stimulation generation circuitry 202 generates therapeutic electrical stimulation signals in accordance with the electrical parameters noted above. For example, processing circuitry 210 may utilize the example techniques described in this disclosure to determine the parameters for the therapeutic electrical stimulation signals (e.g., based on evaluation of evoked signals 216), and stimulation generation circuitry 202 may deliver the therapeutic electrical stimulation signals. Other ranges of therapy parameter values may also be useful, and may depend on the target stimulation site within patient 112. While stimulation pulses are described, stimulation signals may be of any form, such as continuous-time signals (e.g., sine waves) or the like.

In addition to delivering therapeutic electrical stimulation signals, stimulation generation circuitry 202 may be configured to deliver electrical stimulation signals for evoking evoked signals (e.g., where information indicative of the evoked signals are stored as evoked signals 216). Example parameters of the electrical stimulation signals for evoking evoked signals include amplitude within range of 0 to 7.5 mA, such as 0 to 5 mA, frequency within range of 5 Hz to 250 Hz, such as less than 80 to 220 Hz, and pulse width in range of 6 to 450 microseconds, such as 60 to 120 microseconds.

Processing circuitry 210 may include fixed function processing circuitry and/or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 may control stimulation generation circuitry 202 according to therapy programs stored in memory 212 to apply particular parameter values specified by one or more of programs, such as voltage amplitude or current amplitude, pulse width, and/or pulse rate.

In the example shown in FIG. 2, the set of electrodes 116 includes electrodes 116A, 116B, 116C, and 116D, and the set of electrodes 118 includes electrodes 118A, 118B, 118C, and 118D. Processing circuitry 210 also controls stimulation generation circuitry 202 to generate and apply the stimulation signals to selected combinations of electrodes 116, 18. Stimulation generation circuitry 202 includes a plurality of pairs of voltage sources, current sources, voltage sinks, or current sinks connected to each of electrodes 116, 118 such that each pair of electrodes has a unique signal circuit. In other words, in these examples, each of electrodes 116, 118 is independently controlled via its own signal circuit (e.g., via a combination of a regulated voltage source and sink or regulated current source and sink), as opposed to switching signals between electrodes 116, 118.

Sensing circuitry 204 is configured to monitor signals from any combination of electrodes 116, 118. Although sensing circuitry 204 is incorporated into a common housing with stimulation generation circuitry 202 and processing circuitry 210 in FIG. 2, in other examples, sensing circuitry 204 may be in a separate housing from IMD 106 and may communicate with processing circuitry 210 via wired or wireless communication techniques.

Figure 4:
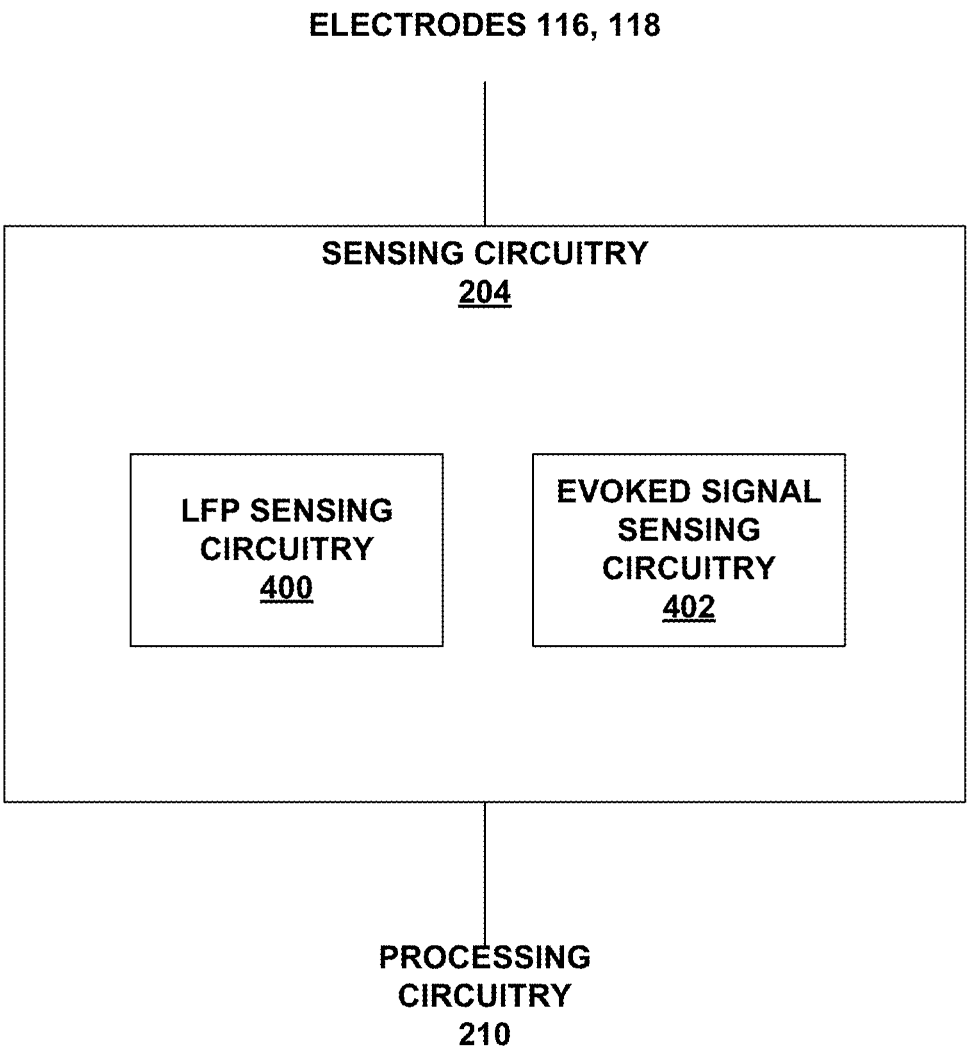
FIG. 4 is a block diagram illustrating an example of a sensing circuitry of FIG. 2 in further detail.

In some examples, sensing circuitry 204 includes one or more amplifiers, filters, and analog-to-digital converters. Sensing circuitry 204 may be used to sense physiological signals, such as LFP measurements for storage as LFP measurements 214 and evoked signals for storage as evoked signals 216. In some examples, sensing circuitry 204 measures LFP and evoked signals from a particular combination of electrodes 116, 118. In some cases, the particular combination of electrodes for sensing includes different electrodes than a set of electrodes 116, 118 used to deliver electrical stimulation signals (e.g., therapeutic electrical stimulation signals or electrical stimulation signals for evoking the evoked signals). Alternatively, in other cases, the particular combination of electrodes used for sensing includes at least one of the same electrodes as a set of electrodes used to deliver stimulation signals to patient 120. Sensing circuitry 204 may provide signals to an analog-to-digital converter, for conversion into a digital signal for processing, analysis, storage, or output by processing circuitry 210. An example of sensing circuitry 204 is illustrated in FIG. 4.

Electrodes 116, 118 on respective leads 114 may be constructed of a variety of different designs. For example, one or both of leads 114 may include two or more electrodes at each longitudinal location along the length of the lead, such as multiple electrodes, e.g., arranged as segments, at different perimeter locations around the perimeter of the lead at each of the locations A, B, C, and D. FIGS. 5A and 5B illustrate such example leads.

As an example, one or both of leads 114 may include circumferentially-segmented DBS arrays of electrodes and non-segmented electrodes (e.g., ring electrodes). As one example, there may be a first ring electrode of electrodes 116 around the perimeter of lead 114A at a first longitudinal location on lead 114A (e.g., location A). Below the first ring electrode, there may be three segmented electrodes of electrodes 116 around the perimeter of lead 114A at a second longitudinal location on lead 114A (e.g., location B). Below the three segmented electrodes, there may be another set of three segmented electrodes of electrodes 116 around the perimeter of lead 114A at a third longitudinal location of lead 114A (e.g., location C). Below the three segmented electrodes, there may be a second ring electrode of electrodes 116 around the perimeter of lead 114A (e.g., location D). Electrodes 118 may be similarly positioned along lead 114B.

The above is one example of the array of electrodes, and the example techniques should not be considered limited to such an example. There may be other configurations of electrodes for DBS. Moreover, the example techniques are not limited to DBS, and other electrode configurations are possible.

In one example, the electrodes 116, 118 may be electrically coupled to stimulation generation circuitry 202 and sensing circuitry 204 via respective wires that are straight or coiled within the housing of the lead and run to a connector at the proximal end of the lead. In another example, each of the electrodes 116, 118 of the leads 114 may be electrodes deposited on a thin film. The thin film may include an electrically conductive trace for each electrode that runs the length of the thin film to a proximal end connector. The thin film may then be wrapped (e.g., a helical wrap) around an internal member to form the leads 114. These and other constructions may be used to create a lead with a complex electrode geometry.

Telemetry circuitry 208 supports wireless communication between IMD 106 and an external programmer 104 or another computing device under the control of processing circuitry 210. Processing circuitry 210 of IMD 106 may receive, as updates to programs, values for various parameters such as magnitude and electrode combination, from programmer 104 via telemetry circuitry 208. The updates to the therapy programs may be stored within therapy programs 214 portion of memory 211. Telemetry circuitry 208 in IMD 106, as well as telemetry modules in other devices and systems described herein, such as programmer 104, may accomplish communication by radiofrequency (RF) communication techniques. In addition, telemetry circuitry 208 may communicate with external medical device programmer 104 via proximal inductive interaction of IMD 106 with programmer 104. Accordingly, telemetry circuitry 208 may send information to external programmer 104 on a continuous basis, at periodic intervals, or upon request from IMD 106 or programmer 104.

Power source 220 delivers operating power to various components of IMD 106. Power source 220 may include a small rechargeable or non-rechargeable battery and a power generation circuit to produce the operating power. Recharging may be accomplished through proximal inductive interaction between an external charger and an inductive charging coil within IMD 104. In some examples, power requirements may be small enough to allow IMD 104 to utilize patient motion and implement a kinetic energy-scavenging device to trickle charge a rechargeable battery. In other examples, traditional batteries may be used for a limited period of time.

The DBS therapy is defined by one or more therapy programs 214 having one or more parameters stored within memory 211. For example, the one or more parameters include a current amplitude (for a current-controlled system) or a voltage amplitude (for a voltage-controlled system), a pulse rate or frequency, and a pulse width, or a number of pulses per cycle. In examples where the electrical stimulation is delivered according to a "burst" of pulses, or a series of electrical pulses defined by an "on-time" and an "off-time," the one or more parameters may further define one or more of a number of pulses per burst, an on-time, and an off-time. Processing circuitry 210, via electrodes 116, 118, delivers DBS to patient 120 and may adjust one or more parameters defining the electrical stimulation based on corresponding parameters of the sensed one or more signals of brain 120.

In some examples, processing circuitry 210 continuously measures the one or more LFP in real time. In other examples, processing circuitry 210 periodically samples the one or more LFP according to a predetermined frequency or after a predetermined amount of time. In some examples, processing circuitry 210 periodically samples the signal at a frequency of approximately 150 Hertz. In some examples, processing circuitry 210 may determine evoked signals periodically, or according to a predetermined schedule.

According to the techniques of the disclosure, processing circuitry 210 may be configured to determine which electrodes 116, 118 should be used to deliver electrical stimulation, and configured to determine parameters for the therapeutic electrical stimulation. To determine which electrodes 116, 118 to use for delivering electrical stimulation, processing circuitry 210 may determine a plurality of LFP measurements of an LFP. In some examples, each of the LFP measurements is measured with different electrodes 116, 118 on a lead 114A, 114B. Processing circuitry 210 may store the LFP measurements as LFP measurements 214. Processing circuitry 210 may determine one or more electrodes 116, 118 on lead 114A, 114B for delivering therapeutic electrical stimulation signal based on the LFP measurements (e.g., by retrieving and evaluating LFP measurements 214).

As one example, processing circuitry 210 may determine which electrodes 116, 118 have the greatest current source density (CSD) value due to sensing of the LFP. However, other techniques to determine which electrodes 116, 118 to use to deliver electrical stimulation are possible. For example, to determine the one or more electrodes 116, 118 on lead 114A, 114B that for delivering therapeutic electrical stimulation signal based on the LFP measurements, processing circuitry 210 may be configured to determine an LFP measurement from the plurality of LFP measurements having a highest powered signal in one or more of a 4-8 Hertz (Hz) band (e.g., theta band), 8-33 Hz band (e.g., beta band), or 35-100 Hz band (e.g., gamma band), and determine the one or more electrodes based on the LFP measurement having the highest powered signal in the 4-8 Hz band, 8-33 Hz band, or 35-100 Hz band.

In addition to determining which electrodes to use to deliver the therapeutic electrical stimulation, in some examples, processing circuitry 210 may be configured to determine parameters for the therapeutic electrical stimulation signal. For ease of description, the following is described with respect to determining a frequency of the therapeutic electrical stimulation. The example techniques may be applicable to other electrical parameters such as amplitude and pulse width.

Processing circuitry 210 may control stimulation generation circuitry 202 to deliver a plurality of electrical stimulation signals via the determined one or more electrodes 116, 118. The plurality of electrical stimulation signals each include at least one different therapy parameter. For example, processing circuitry 210 may control stimulation generation circuitry 202 to deliver a plurality of electrical stimulation signals to evoke evoked potential signals or to evoke ERNA signals. For example, processing circuitry 210 may control stimulation generation circuitry 202 to deliver a plurality of electrical stimulation signals, where two or more of the plurality of electrical stimulation signals has a different amplitude within a particular range (e.g., 0 mA to 7.5 mA). In this example, the frequency of each of the plurality of electrical signals may be less than a threshold frequency (e.g., less than 80 Hz). The evoked signals in this example may be evoked potential signals. As another example, processing circuitry 210 may control stimulation generation circuitry 202 to deliver a plurality of electrical stimulation signals, where two or more of the plurality of electrical stimulation signals has a different frequency within a particular range (e.g., between 80 to 220 Hz with 5 Hz increments). For example, a frequency of two or more of the plurality of electrical stimulation signals is different. For instance, a first electrical stimulation signal of the plurality of electrical stimulation signals is different than a frequency of a second electrical stimulation signal of the plurality of electrical stimulation signals. In this example, the frequency of each of the plurality of electrical signals may be higher than a threshold frequency (e.g., 80 Hz). The evoked signals in this example may be ERNA signals.

As another example, processing circuitry 210 may control stimulation generation circuitry 202 to deliver a first plurality of electrical stimulation signals, where a frequency of each of the first plurality of electrical stimulation signals is lower than a threshold frequency, where at least one of an amplitude or pulse width of two or more of the first plurality of electrical stimulation signals is different (e.g., an amplitude or pulse width of a first electrical stimulation signal of the first plurality of electrical stimulation signals is different than an amplitude or pulse width of a second electrical stimulation signal of the first plurality of electrical stimulation signals), and the evoked signals, that are evoked from delivery of the first plurality of electrical stimulation signals, are evoked potential signals. Processing circuitry 210 may control stimulation generation circuitry 202 to deliver a second plurality of electrical stimulation signals, where a frequency of two or more of the second plurality of electrical stimulation signals is different (e.g., a frequency of a first electrical stimulation signal of the second plurality of electrical stimulation signals is different than a frequency of a second electrical stimulation signal of the second plurality of electrical stimulation signals). For respective ones of the second plurality of electrical stimulation signals, processing circuitry 210 may determine respective evoked resonant neural activity (ERNA) signals, where the respective ERNA signals are evoked by delivery of the respective second plurality of electrical stimulation signals.

In some examples, processing circuitry 210 may control stimulation generation circuitry 202 to deliver the second plurality of electrical stimulation signals, where an amplitude or pulse width of two or more of the plurality of electrical stimulation signals is different (e.g., an amplitude or pulse width of a first electrical stimulation signal of the plurality of electrical stimulation signals is different than an amplitude or pulse width of a second electrical stimulation signal of the plurality of electrical stimulation signals). For respective ones of the second plurality of electrical stimulation signals, processing circuitry 210 may determine respective ERNA signals.

As described, for respective ones of the plurality of electrical stimulation signals, processing circuitry 210 may determine respective evoked signals (e.g., information of the evoked signals is stored as evoked signals 216). The respective evoked signals may be evoked by delivery of the respective plurality of electrical stimulation signals.

Processing circuitry 210 may determine parameters for the therapeutic electrical stimulation signal based on the respective evoked signals. For example, the evoked signals may be evoked potential signals. Processing circuitry 210 may select an evoked potential signal from the respective evoked potential signals based on amplitude, peak latency, or trough latency of the respective evoked potential signals, and determine an electrical stimulation signal from the plurality of electrical stimulation signals based on the selected evoked potential signal. Peak latency may refer to when a peak occurs in the evoked potential signal, such as a difference between the when the peak occurs and a target timing of when the peak should occur. Similarly, trough latency may refer to when a trough occurs in the evoked potential signal, such as a difference between the when the trough occurs and a target timing of when the trough should occur.

For instance, processing circuitry 210 may determine the respective electrical stimulation signal that evoked the selected evoked potential signal. Processing circuitry 210 may determine parameters of the determined electrical stimulation signal, and to determine at least one parameter for the therapeutic electrical stimulation signal, processing circuitry 210 is configured to determine at least one parameter for the therapeutic electrical stimulation signal based on the determined parameters of the determined electrical stimulation signal.

For example, assume that processing circuitry 210 selected an evoked potential signal based on the amplitude of the evoked potential signal (e.g., the selected evoked potential signal had the greatest amplitude). In this example, processing circuitry 210 may determine that the electrical stimulation signal having an amplitude of 1 mA evoked the selected evoked potential signal. Processing circuitry 210 may determine the amplitude of the therapeutic electrical stimulation signal based on the amplitude of the electrical stimulation signal that evoked the selected evoked potential signal. For instance, processing circuitry 210 may determine the amplitude of the therapeutic electrical stimulation signal to be 1 mA.

As another example, processing circuitry 210 may be configured to select an ERNA signal from the respective ERNA signals based on resonant activity of the respective ERNA signals. The resonant activity of the respective ERNA signals may include one or more of peak-to-trough amplitude, time between peak-to-peak, change in peak amplitudes, amount of oscillations, rise or fall times, and frequency shift from early resonance to late resonance of the respective ERNA signals. Processing circuitry 210 may determine an electrical stimulation signal from the plurality of electrical stimulation signals based on the selected ERNA signal. For instance, processing circuitry 210 may determine the respective electrical stimulation signal that evoked the selected ERNA signal. Processing circuitry 210 may determine parameters of the determined electrical stimulation signal, and to determine at least one parameter for the therapeutic electrical stimulation signal, processing circuitry 210 may be configured to determine at least one parameter for the therapeutic electrical stimulation signal based on the determined parameters of the determined electrical stimulation signal.

For example, assume that processing circuitry 210 selected an ERNA based on the resonant activity of the ERNA signal (e.g., the selected ERNA signal had the highest number of oscillations, fastest rise or fall time, highest peak-to-trough amplitude, or some other resonant activity of interest). In this example, processing circuitry 210 may determine that the electrical stimulation signal having a frequency of 130 Hz evoked the selected ERNA signal. Processing circuitry 210 may determine the frequency of the therapeutic electrical stimulation signal based on the frequency of the electrical stimulation signal that evoked the selected ERNA signal. For instance, processing circuitry 210 may determine the frequency of the therapeutic electrical stimulation signal to be 130 Hz.

Processing circuitry 210 may output information indicative of the determined at least one parameter. For example, processing circuitry 210 may output the information indicative of the determined at least one parameter to programmer 104, or may output the information indicative of the determined at least one parameter to stimulation generation circuitry 202. In some examples, processing circuitry 210 may output the information indicative of the at determined at least one parameter for storage in memory 212 as part of a therapy program. In some examples, processing circuitry 210 may be configured to control stimulation generation circuitry 202 to deliver the therapeutic electrical stimulation signal based on the determined at least one parameter.

There may be benefit in using ERNA signals for determining the parameters for the therapeutic electrical stimulation signal, as compared to other signals such as LFP measurements. As one example, LFP measurements may be less reliable in cases of high ECG artifact. For instance, ECG signals may impact measurements of LFP more than ERNA signals.

Accordingly, the LFP measurements may be well suited for determining which electrodes to use for stimulation (e.g., even in instances where there is ECG artifact), and ERNA signals may be well suited for determining parameters for the therapeutic electrical stimulation signals.

Although ERNA signals may be useful for determining parameters for the therapeutic electrical stimulation signals, in some examples, processing circuitry 210 may determine whether to use ERNA signals based on information from another sensor. As an example, output from an accelerometer (not shown) in IMD 106 may indicate the posture of patient 112. The reliability of the ERNA signals for determining parameters for the therapeutic electrical stimulation signals may be based on posture of patient 112. In some examples, based on the posture information of the patient from the accelerometer, processing circuitry 210 may selectively determine whether to use the ERNA signals for determining parameters for the therapeutic electrical stimulation signals.

In the above examples, LFP measurements are used for determining which electrodes to use for stimulation, and ERNA signals are used for determining parameters for therapeutic electrical stimulation signals. In some examples, processing circuitry 210 may use ERNA signals for determining which electrodes to use for stimulation, and for determining parameters for therapeutic electrical stimulation signals, such as when there is too much noise on the LFP measurements (e.g., due to excessive ECG artifacts). As another example, processing circuitry 210 may use input from another sensor (e.g., accelerometer) to determine reliability of the ERNA signals or LFP measurements. Based on the reliability determination, processing circuitry 210 may use ERNA signals or LFP measurements for determining which electrodes to use for stimulation, and possibly the parameters for therapeutic electrical stimulation signals.

Figure 3:
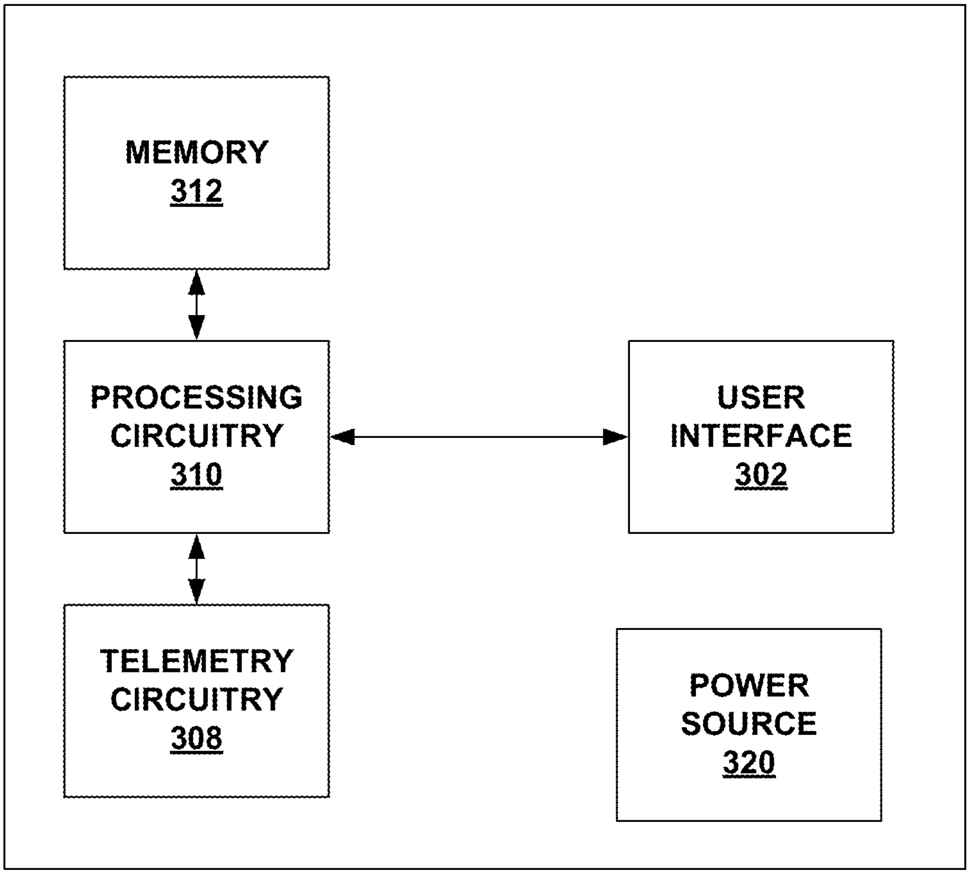
FIG. 3 is a block diagram of the external programmer of FIG. 1 for controlling delivery of DBS therapy according to an example of the techniques of the disclosure.

FIG. 3 is a block diagram of the external programmer 104 of FIG. 1. Although programmer 104 may generally be described as a hand-held device, programmer 104 may be a larger portable device or a more stationary device. In addition, in other examples, programmer 104 may be included as part of an external charging device or include the functionality of an external charging device. As illustrated in FIG. 3, programmer 104 may include processing circuitry 310, memory 312, user interface 302, telemetry circuitry 308, and power source 320. Memory 312 may store instructions that, when executed by processing circuitry 310, cause processing circuitry 310 and external programmer 104 to provide the functionality ascribed to external programmer 104 throughout this disclosure. Each of these components, or modules, may include electrical circuitry that is configured to perform some or all of the functionality described herein. For example, processing circuitry 310 may include processing circuitry configured to perform the processes discussed with respect to processing circuitry 310.

In general, programmer 104 comprises any suitable arrangement of hardware, alone or in combination with software and/or firmware, to perform the techniques attributed to programmer 104, and processing circuitry 310, user interface 302, and telemetry circuitry 308 of programmer 104. In various examples, programmer 104 may include one or more processors, which may include fixed function processing circuitry and/or programmable processing circuitry, as formed by, for example, one or more microprocessors, DSPs, ASICs, FPGAs, or any other equivalent integrated or discrete logic circuitry, as well as any combinations of such components. Programmer 104 also, in various examples, may include a memory 312, such as RAM, ROM, PROM, EPROM, EEPROM, flash memory, a hard disk, a CD-ROM, comprising executable instructions for causing the one or more processors to perform the actions attributed to them. Moreover, although processing circuitry 310 and telemetry circuitry 308 are described as separate modules, in some examples, processing circuitry 310 and telemetry circuitry 308 may be functionally integrated with one another. In some examples, processing circuitry 310 and telemetry circuitry 308 correspond to individual hardware units, such as ASICs, DSPs, FPGAs, or other hardware units.

Memory 312 (e.g., a storage device) may store instructions that, when executed by processing circuitry 310, cause processing circuitry 310 and programmer 104 to provide the functionality ascribed to programmer 104 throughout this disclosure. For example, memory 312 may include instructions that cause processing circuitry 310 to obtain a parameter set from memory or receive a user input and send a corresponding command to IMD 106, or instructions for any other functionality. In addition, memory 312 may include a plurality of programs, where each program includes a parameter set that defines stimulation therapy.

User interface 302 may include a button or keypad, lights, a speaker for voice commands, a display, such as a liquid crystal (LCD), light-emitting diode (LED), or organic light-emitting diode (OLED). In some examples the display may be a touch screen. User interface 302 may be configured to display any information related to the delivery of stimulation therapy, identified patient behaviors, sensed patient parameter values, patient behavior criteria, or any other such information. User interface 302 may also receive user input via user interface 302. The input may be, for example, in the form of pressing a button on a keypad or selecting an icon from a touch screen.

Telemetry circuitry 308 may support wireless communication between IMD 106 and programmer 104 under the control of processing circuitry 310. Telemetry circuitry 308 may also be configured to communicate with another computing device via wireless communication techniques, or direct communication through a wired connection. In some examples, telemetry circuitry 308 provides wireless communication via an RF or proximal inductive medium. In some examples, telemetry circuitry 308 includes an antenna, which may take on a variety of forms, such as an internal or external antenna.

Examples of local wireless communication techniques that may be employed to facilitate communication between programmer 104 and IMD 106 include RF communication according to the 802.11 or Bluetooth specification sets or other standard or proprietary telemetry protocols. In this manner, other external devices may be capable of communicating with programmer 104 without needing to establish a secure wireless connection.

In some examples, processing circuitry 310 of external programmer 104 defines the parameters of electrical stimulation therapy, stored in memory 312, for delivering DB S to patient 120. In one example, processing circuitry 310 of external programmer 104, via telemetry circuitry 308, issues commands to IMD 106 causing IMD 106 to deliver electrical stimulation therapy via electrodes 116, 118 via leads 114.

In one or more examples, programmer 104 may be configured to perform one or more of the example techniques described in this disclosure. For instance, processing circuitry 310 may be configured to perform one or more of the example operations described above with respect to processing circuitry 210.

FIG. 4 is a block diagram illustrating an example of a sensing circuitry of FIG. 2 in further detail. As illustrated in FIG. 4, sensing circuitry 204 includes LFP sensing circuitry 400 and evoked signal sensing circuitry 402. LFP sensing circuitry 400 may be configured to specifically determine LFP measurements, and evoked signal sensing circuitry 402 may be configured to specifically sense evoked signals (e.g., evoked potential signals and/or ERNA signals).

For instance, an LFP can generally be measured at any time, including instances when IMD 106 is delivered electrical stimulation (e.g., therapeutic electrical stimulation signals or electrical stimulation signals that evoke the evoked signals). This is because the LFP is intrinsically generated by a signal source (e.g., one or more neurons) within brain 120 of patient 122. Accordingly, LFP sensing circuitry 400 may be configured to continuously determine LFP measurements, periodically determine LFP measurements, or determine LFP measurements in accordance with a schedule irrespective of when stimulation generation circuitry 202 is configured to deliver the stimulation (e.g., therapeutic electrical stimulation signals or electrical stimulation signals that evoke the evoked signals).

Evoked signal sensing circuitry 402 may, however, sense evoked signals in response to delivery of an electrical stimulation signal. Accordingly, during the time the electrical stimulation signal is being delivered, and prior to the delivery of the electrical stimulation signal, evoked signal sensing circuitry 402 may be configured to not sense evoked signals.

Furthermore, in response to delivery of an electrical stimulation signal, the signal that sensing circuitry 204 senses may be a composite signal includes at least two components. The first component is the evoked signal that is evoked due to the delivery of the electrical stimulation signal (e.g., evoked potential signal if frequency of stimulation signal less than threshold frequency, and ERNA signal if frequency of stimulation signal greater than threshold frequency). The second component may be the LFP, which may still be present even with delivery of the electrical stimulation signal that evoked the evoked signal because such electrical stimulation signal may not be therapeutic.

Accordingly, processing circuitry 210 may be configured to differentiate between the LFP measurement and the evoked signal in such a composite signal. In some examples, LFP sensing circuitry 400 may be configured to filter out signals that are out of the frequency band of the LFP band of interest (e.g., outside of the beta band). Evoked signal sensing circuitry 402 may be similarly configured to filter out signals that are out of the frequency band of evoked signals (e.g., filter out signals outside the 270 to 340 Hz range). Accordingly, processing circuitry 210 may receive the LFP measurements from LFP sensing circuitry 400 and the evoked signals from evoked signal sensing circuitry 402.

The example of sensing circuitry 204 of FIG. 4 is one example, and should not be considered limiting. In some examples, sensing circuitry 204 may not necessarily include LFP sensing circuitry 400 and evoked signal sensing circuitry 402. In such examples, processing circuitry 210 may receive the composite signal that includes both the LFP and the evoked signals, when an electrical stimulation signal that evokes the evoked signals is delivered by stimulation generation circuitry 202. To differentiate between the evoked signals and the LFP, processing circuitry 210 may be configured to determine the LFP measurement immediately before stimulation generation circuitry 202 delivers electrical stimulation that evokes an evoked signal. Then, when processing circuitry 210 receive the composite signal that includes the LFP and the evoked signal, processing circuitry 210 may subtract the LFP measurement taken immediately before stimulation circuitry 202 delivered electrical stimulation that evoked the evoked signal from the composite signal to determine the evoked signal.

FIGS. 5A and 5B are conceptual diagrams illustrating examples of leads that configured to be implanted within a brain of a patient. FIGS. 6A and 6B are conceptual diagrams illustrating examples of local field potential (LFP) measurements from different electrodes. The examples of FIGS. 5A, 5B, 6A, and 6B are described together to ease with understanding. In FIG. 5A, lead 506A includes electrodes 502A and 502D (e.g., ring electrodes) and group of electrodes 502B and group of electrodes 502C. In FIG. 5B, lead 506B includes electrodes 504A and 504D (e.g., ring electrodes) and group of electrodes 504B and group of electrodes 504C. Leads 506A and 506B may be substantially similar, including the same as, leads 114A, 114B. Group of electrodes 502B, 502C, 504B, and 504C each represent a grouping of three segment electrodes on the perimeter of leads 506A, 506B. For example, group of electrodes 502B includes a first, second, and third segment electrode, and same for group of electrodes 502C, 504B, and 504C.

In one or more examples, electrodes 502A-502D and electrodes 504A-504D may be considered at different respective levels. For example, electrodes 502D and 504D may be considered to be at level 0, group of electrodes 502C and 504C may be considered to be at level 1, group of electrodes 502B and 504B may be considered to be at level 2, and electrodes 502A and 504A may be considered to be at level 3.

For example, as shown in FIG. 5A, electrodes 502A, 502D, and group of electrodes 502C, 502B may be considered at different levels. For instance, ring electrode is at level E0, and ring electrode 502A is at level E3. Group of electrodes 502C is at level E1 and includes electrodes E1*a*, E1*b*, and E1*c*. Group of electrodes 502B is at level E2 and includes electrodes E2*a*, E2*b*, and E2*c*. Although not shown in FIG. 5B, electrodes 504A, 504D and group of electrodes 504C, 504B may be considered to be at different levels, similar to the example illustrated in FIG. 5A.

In some examples, processing circuitry 210 may cause each of the segmented electrode in group of electrodes 502B to be coupled together to create an effective ring electrode. Processing circuitry 210 may perform similar operations for group of electrodes 502C. Processing circuitry 210 may set one of the electrodes on lead 506B (e.g., electrode 504A) and determine LFP measurements between respective electrodes 502 at different levels and reference electrode 504A.

FIG. 6A illustrates an example of the results of the LFP measurements. For example, E0 refers to level E0 shown in FIG. 5A, and indicates the LFP measurement between electrode 502D and 504A, which is 0.232 μVpeak. E1 refers to level E1 shown in FIG. 5A, and indicates the LFP measurement between the effective ring electrode from group of electrodes 502C and 504A, which is 1.146 μVpeak. E2 refers to level E2 shown in FIG. 5A, and indicates the LFP measurement between the effective ring electrode from group of electrodes 502B and 504A, which is 0 μVpeak. E3 refers to level E3 shown in FIG. 5A, and indicates the LFP measurement between electrode 502A and 504A, which is 0.1587 μVpeak.

In the example of FIG. 6A, because the LFP measurement for level E1, which corresponds to group of electrodes 502C, was the highest, processing circuitry 210 may determine the LFP measurements for respective ones of the electrodes in the group of electrodes 502C. FIG. 6B illustrates the results for the LFP measurements for respective ones of the electrodes in the group of electrodes 502C, and also illustrates the results for the LFP measurements for respective ones of the electrodes in the group of electrodes 502B in the event that the LFP signal source happened to be in between group of electrodes 502C and 502B.

In FIG. 6B, E1*a* refers to a first segmented electrode in group of electrodes 502C, E1*b* refers to a second segmented electrode in group of electrodes 502C, and E1*c* refers to a third segmented electrode in group of electrodes 502C. E2*a* refers to a first segmented electrode in group of electrodes 502B, E2*b* refers to a second segmented electrode in group of electrodes 502B, and E2*c* refers to a third segmented electrode in group of electrodes 502B.

As shown in FIG. 6B, the LFP measurement for the third electrode segment in group of electrodes 502C is the highest. Therefore, processing circuitry 210 may determine that the third electrode segment in group of electrodes 502C is to be used for delivery of therapeutic electrical stimulation signals. Moreover, processing circuitry 210 may control stimulation generation circuitry 202 to deliver a plurality of electrical stimulation signals via the determined one or more electrodes (e.g., via the third electrode segment in group of electrodes 502C).

The example of FIGS. 5A, 5B, 6A, and 6B should not be considered limiting. For instance, in some examples, processing circuitry 210 may not first create effective ring electrodes to determine the LFP measurements as shown in FIG. 6A before determining the LFP measurements as shown in FIG. 6B. Rather, processing circuitry 210 may determine the LFP measurements of each ring electrode and each segmented electrode, and select the LFP measurement from the LFP measurements.

In some examples, processing circuitry 210 may use evoked signals to determine which electrode(s) to use for stimulation (e.g., in addition to or instead of using LFP measurements). As an example, processing circuitry 210 may utilize the evoked signals to confirm that the electrodes selected using the LFP measurements are the correct electrodes to use for stimulation.

Processing circuitry 210 may receive information for sensed evoked signals on a plurality of pairs of electrodes to determine which electrodes are proximate to the signal source (e.g., based on amplitude or other signal characteristics of the evoked signals). Processing circuitry 210 may determine whether the pairs of electrodes that are proximate to the signal source, as determined using evoked signals, are the same as the electrodes selected to be used for stimulation using the LFP measurements, such as for confirmation. If the electrodes selected using the LFP measurements for stimulation and the electrodes determined using evoked signals for stimulation are different, processing circuitry 210 may utilize some confidence scoring to determine whether to use the electrodes determined from LFP measurements or evoked signals. As another example, processing circuitry 210 may select a pair of electrodes, to be used for stimulation, that are equally proximate to both the electrodes determined using LFP measurement and electrodes determine using evoked signals. Other ways in which to select which electrodes to use for stimulation if the electrodes selected using LFP measurements for stimulation and the electrodes selected using evoked signals for stimulation are different.

Figure 7A:
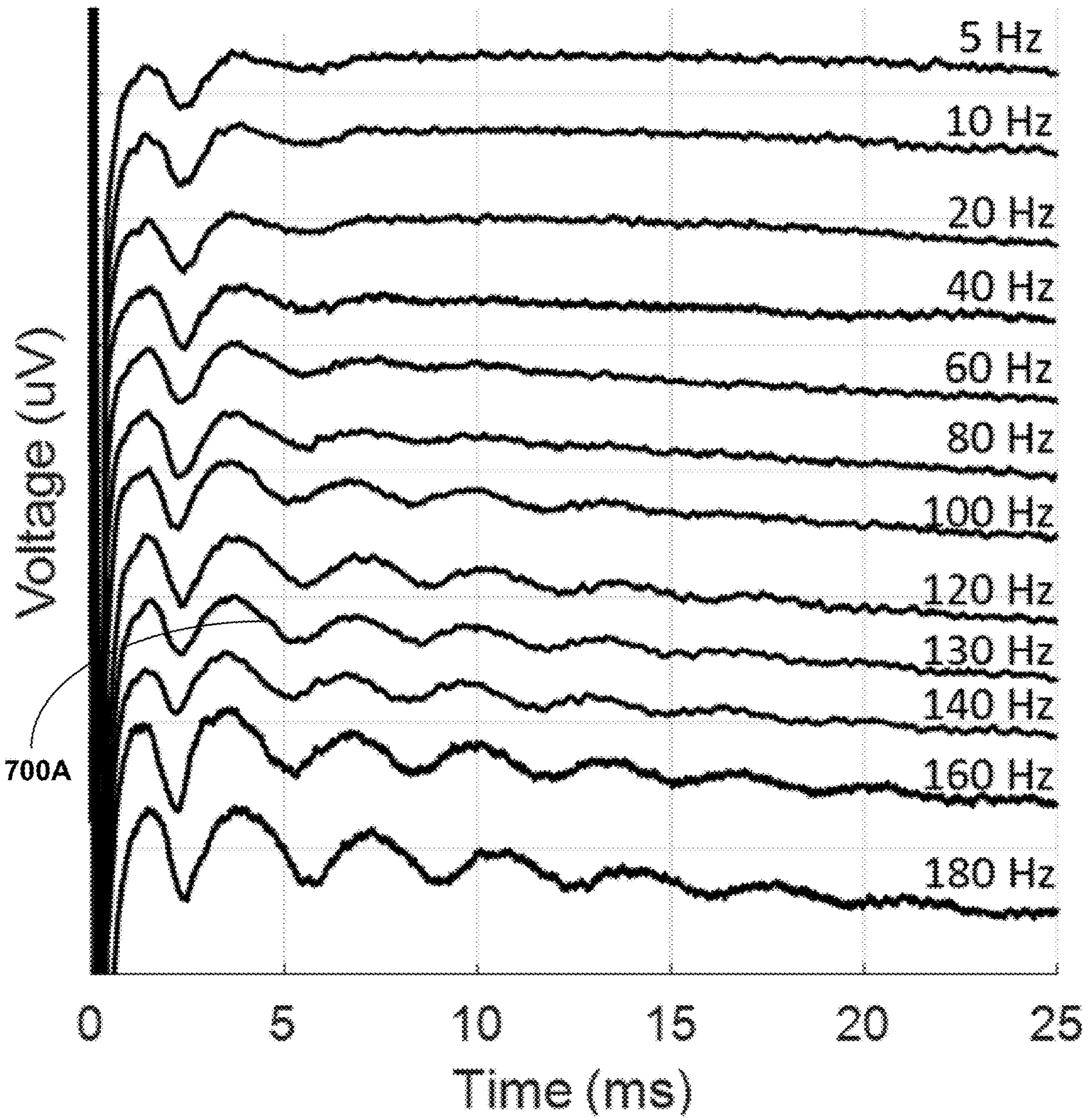
FIGS. 7A and 7B are graphs illustrating evoked resonant neural activity (ERNA) signals generated with electrical stimulation delivered at different frequencies.
Figure 7B:
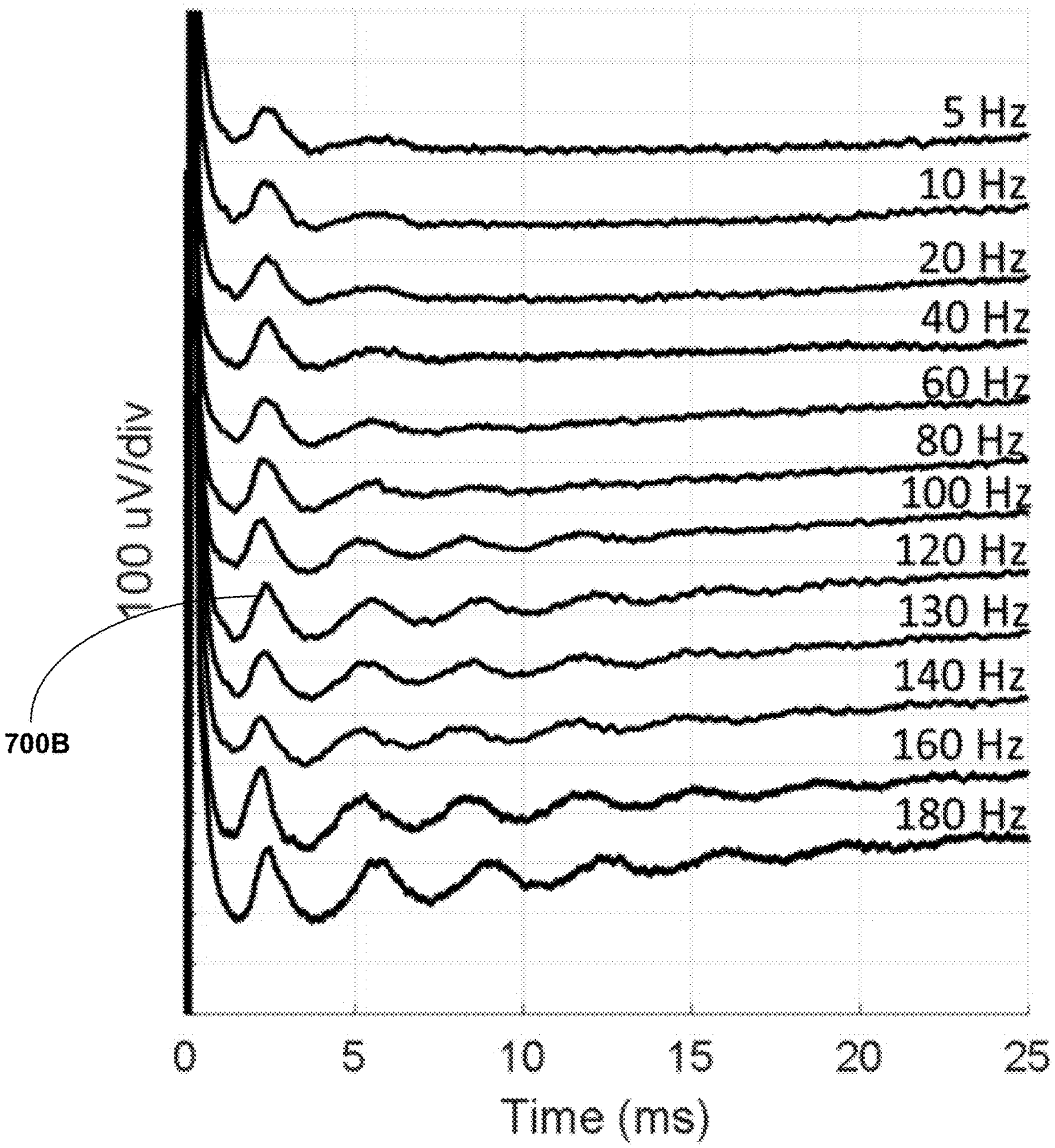

FIGS. 7A and 7B are graphs illustrating evoked resonant neural activity (ERNA) signals generated with electrical stimulation delivered at different frequencies. For instance, as described above, for respective ones of the plurality of electrical stimulation signals that stimulation generation circuitry 202 delivers, processing circuitry 210 may determine respective ERNA signals, where the respective ERNA signals are evoked by delivery of the respective plurality of electrical stimulation signals. FIGS. 7A and 7B illustrate examples of the respective ERNA signals.

For instance, in FIGS. 7A and 7B, stimulation generation circuitry 202 may deliver the electrical stimulation signals between the third segment electrode of group of electrodes 502C and the housing of IMD 106, and may sense the ERNA signals between electrodes 502D and 504A. The amplitude of the electrical stimulation signals may be 1 milli-Amp (1 mA), and the pulse width of the stimulation signals may be 120 micro-seconds. As illustrated, the first ERNA signal in FIGS. 7A and 7B is the ERNA signal evoked by delivery of an electrical stimulation signal having a frequency of 5 Hz. The second ERNA signal in FIGS. 7A and 7B is the ERNA signal evoked by delivery of an electrical stimulation signal having a frequency of 10 Hz, and so forth.

In one or more examples, processing circuitry 210 may store the example ERNA signals of FIGS. 7A and 7B as ERNA signals of evoked signals 216 for evaluation. For instance, processing circuitry 210 may retrieve ERNA signals of evoked signals 216 and select an ERNA signal from the respective ERNA signals based on resonant activity of the respective ERNA signals. The resonant activity of the respective ERNA signals may include one or more of peak-to-trough amplitude, time between peak-to-peak, change in peak amplitudes, amount of oscillations, rise or fall times, and frequency shift from early resonance to late resonance of the respective ERNA signals. For instance, assume that processing circuitry 210 selected ERNA signal 700A (FIG. 7A) or 700B (FIG. 7B) because the resonant response of ERNA signal 700A or 700B correlated with ERNA signals for patients whose disorder is being managed.

Processing circuitry 210 may determine an electrical stimulation signal from the plurality of electrical stimulation signals based on the selected ERNA signal. For instance, in FIGS. 7A and 7B, processing circuitry 210 may determine the electrical stimulation signal that evoked ERNA signal 700A or 700B. Processing circuitry 210 may determine parameters of the determined electrical stimulation signal. In the example of FIGS. 7A and 7B, processing circuitry 210 may determine that the frequency parameter of the electrical stimulation signal that evoked ERNA signal 700A or 700B is 130 Hz. Accordingly, to determine parameters for the therapeutic electrical stimulation signal, processing circuitry 210 may be configured to determine parameters for the therapeutic electrical stimulation signal based on the determined parameters of the determined electrical stimulation signal. As an example, processing circuitry 210 may determine the frequency of the therapeutic electrical stimulation signal to be 130 Hz.

In the example of FIGS. 7A and 7B, the electrodes used for sensing the ERNA signals was set to be between electrodes 502D and 504A. However, in some examples, processing circuitry 210 may determine which electrodes to use for sensing the ERNA signals. For example, processing circuitry 210 may sense ERNA signals on various different pairs of electrodes of leads 506A, 506B, and based on the resonant activity of the ERNA signals, may select which electrodes to use for sensing the ERNA signals. An example of selecting which electrodes to use for sensing the ERNA signals is illustrated with respect to FIGS. 9A-9G.

As an example, to determine respective ERNA signals, processing circuitry 210 may be configured to receive respective ERNA signals sensed on a plurality of electrodes 502A-502D and 504A-504D on lead 506A, 506B. That is, processing circuitry 210 may determine ERNA signals, similar to those illustrated in FIGS. 7A and 7B but possibly at one frequency, across different pairs of electrodes 502A-502D and 504A-504D. Processing circuitry 210 may select a at least one electrode on lead 506A, 506B for sensing ERNA signals based on the sensed respective ERNA signals. Processing circuitry 210 may select one electrode on leads 506A, 506B and an electrode on the housing of IMD 106 for monopolar sensing, or may select a pair of electrodes on leads 506A, 506B for bipolar sensing. For example, processing circuitry 210 may determine the resonant activity on the ERNA signals, and select the at least one electrode based on the determined resonant activity of the ERNA signals. Processing circuitry 210 may determine the respective ERNA signals from the selected at least one electrode.

Figure 8:
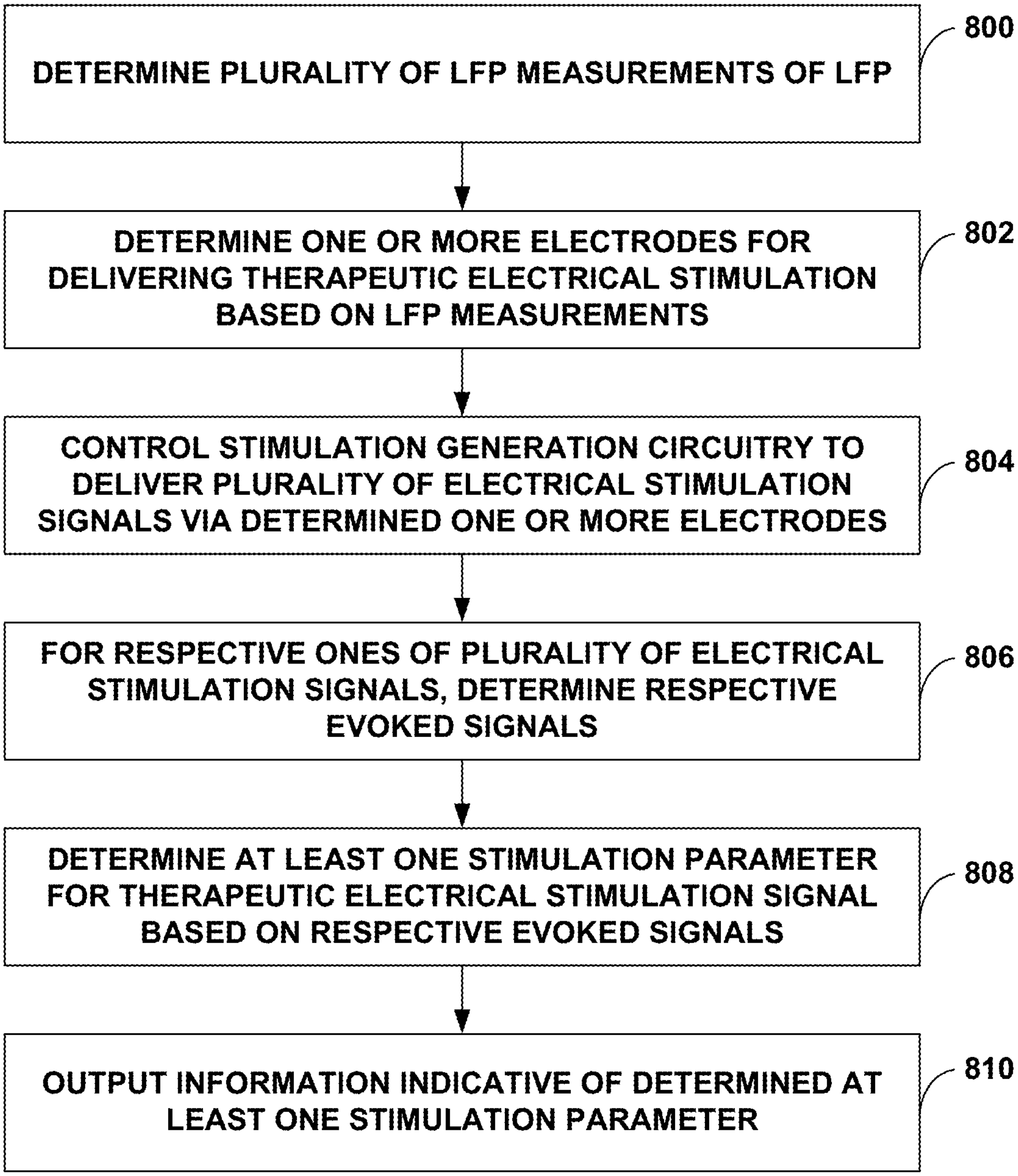
FIG. 8 is a flowchart illustrating an example operation in accordance with techniques of the disclosure.

FIG. 8 is a flowchart illustrating an example operation in accordance with techniques of the disclosure. The example of FIG. 8 is described with respect to processing circuitry. Examples of the processing circuitry includes processing circuitry 210 of IMD 106, processing circuitry 310 of programmer 104, processing circuitry of a cloud computing environment, or any combination thereof. For example, the processing circuitry configured to perform the example operations described for FIG. 8 may be part of IMD 106, programmer 104, or is part of IMD 106, programmer 104, or both IMD 106 and the programmer 104.

The processing circuitry may determine a plurality LFP measurements of an LFP (800). For instance, each of the LFP measurements is measured with different electrodes 116, 118 on lead 114A, 114B. In one or more examples, the LFP is intrinsically generated by a signal source within brain 120 of patient 122.

The processing circuitry may be configured to determine one or more electrodes 116, 118 on lead 114A, 114B for delivering therapeutic electrical stimulation signal based on the LFP measurements (802). For example, to determine the one or more electrodes 116, 118 on lead 114A, 114B for delivering therapeutic electrical stimulation signal based on the LFP measurements, the processing circuitry may be configured to determine an LFP measurement from the plurality of LFP measurements having a highest powered signal in one or more of a 4-8 Hertz (Hz) band, 8-33 Hz band, or 35-100 Hz band, and determine the one or more electrodes based on the LFP measurement having the highest powered signal in the 4-8 Hz band, 8-33 Hz band, or 35-100 Hz band.

The processing circuitry may control stimulation generation circuitry 202 to deliver a plurality of electrical stimulation signals via the determined one or more electrodes (804). The plurality of electrical stimulation signals may each include at least one different therapy parameter (804). For example, the processing circuitry may be configured to control stimulation generation circuitry 202 to deliver the plurality of electrical stimulation signals via the determined one or more electrodes, where an amplitude for each of the plurality of electrical stimulation signals is within a range of amplitudes (e.g., 0.5 mA to 7.5 mA). As another example, the processing circuitry may be configured to control stimulation generation circuitry 202 to deliver the plurality of electrical stimulation signals via the determined one or more electrodes, where a frequency for each of the plurality of electrical stimulation signals is within a range of frequencies (e.g., 80 Hz to 220 Hz).

For respective ones of the plurality of electrical stimulation signals, the processing circuitry may determine respective evoked signals (806). The respective evoked signals are evoked by delivery of the respective plurality of electrical stimulation signals. For instance, the processing circuitry may determine respective ERNA signals such as those illustrated in FIGS. 7A and 7B. As another example, the processing circuitry may determine respective evoked potential signals.

As one example, a frequency of each of the plurality of electrical stimulation signals is lower than a threshold frequency (e.g., less than 80 Hz), an amplitude or pulse width of two or more of the plurality of electrical stimulation signals is different (e.g., an amplitude or pulse width of a first electrical stimulation signal of the plurality of electrical stimulation signals is different than an amplitude or pulse width of a second electrical stimulation signal of the plurality of electrical stimulation signals), and the evoked signals are evoked potential signals. In such examples, to determine at least one parameter for the therapeutic electrical stimulation signal, the processing circuitry is configured to determine at least one of an amplitude or pulse width for the therapeutic electrical stimulation signal based on the evoked potential signals.

As another example, a frequency of each of the plurality of electrical stimulation signals is higher than a threshold frequency (e.g., greater than 80 Hz), an amplitude or pulse width of two or more of the plurality of electrical stimulation signals is different (e.g., an amplitude or pulse width of a first electrical stimulation signal of the plurality of electrical stimulation signals is different than an amplitude or pulse width of a second electrical stimulation signal of the plurality of electrical stimulation signals), and the evoked signals are evoked resonant neural activity (ERNA) signals. In such examples, to determine at least one parameter for the therapeutic electrical stimulation signal, the processing circuitry is configured to determine at least one of an amplitude or pulse width for the therapeutic electrical stimulation signal based on the ERNA signals.

As another example, a frequency of each of the plurality of electrical stimulation signals is higher than a threshold frequency (e.g., greater than 80 Hz), a frequency of two or more of the plurality of electrical stimulation signals is different (e.g., a frequency of a first electrical stimulation signal of the plurality of electrical stimulation signals is different than a frequency of a second electrical stimulation signal of the plurality of electrical stimulation signals), and the evoked signals are ERNA signals. In such examples, to determine at least one parameter for the therapeutic electrical stimulation signal, the processing circuitry is configured to determine a frequency for the therapeutic electrical stimulation signal based on the ERNA signals.

In some examples, the processing circuitry may determine evoked potential signals and ERNA signals for determining parameters for the therapeutic electrical stimulation signal. For example, the plurality of electrical stimulation signals may be a first plurality of electrical stimulation signals, a frequency of each of the first plurality of electrical stimulation signals is lower than a threshold frequency, an amplitude of two or more of the first plurality of electrical stimulation signals is different (e.g., an amplitude or pulse width of a first electrical stimulation signal of the first plurality of electrical stimulation signals is different than an amplitude or pulse width of a second electrical stimulation signal of the first plurality of electrical stimulation signals), and the evoked signals are evoked potential signals. The processing circuitry may be configured to control stimulation generation circuitry 202 to deliver a second plurality of electrical stimulation signals via the determined one or more electrodes, where a frequency of two or more of the second plurality of electrical stimulation signals is different (e.g., a frequency of a first electrical stimulation signal of the second plurality of electrical stimulation signals is different than a frequency of a second electrical stimulation signal of the second plurality of electrical stimulation signals). For respective ones of the second plurality of electrical stimulation signals, the processing circuitry may determine respective ERNA signals, where the respective ERNA signals are evoked by delivery of the respective second plurality of electrical stimulation signals. In such examples, to determine at least one parameter for the therapeutic electrical stimulation signal based on the respective evoked signals, the processing circuitry is configured to determine at least one of an amplitude or pulse width of the therapeutic electrical stimulation signal based on the evoked potential signals, and determine a frequency of the therapeutic electrical stimulation signal based on the ERNA signals.

In this way, the processing circuitry may determine at least one parameter for the therapeutic electrical stimulation signal based on the respective evoked signals (808). For instance, in examples where the evoked signals are evoked potential signals, the processing circuitry may select an evoked potential signal from the respective evoked potential signals based on amplitude, peak latency, or trough latency (as a few non-limiting examples) of the respective evoked potential signals. The processing circuitry may determine an electrical stimulation signal from the plurality of electrical stimulation signals based on the selected evoked potential signal, and determine parameters of the determined electrical stimulation signal. In such examples, to determine at least one parameter for the therapeutic electrical stimulation signal, the processing circuitry may determine at least one parameter for the therapeutic electrical stimulation signal based on the determined parameters of the determined electrical stimulation signal.

As another example, the processing circuitry may be configured to select an ERNA signal from the respective ERNA signals based on resonant activity of the respective ERNA signals. The resonant activity of the respective ERNA signals includes one or more of peak-to-trough amplitude, time between peak-to-peak, change in peak amplitudes, amount of oscillations, rise or fall times, and frequency shift from early resonance to late resonance of the respective ERNA signals.

The processing circuitry may determine an electrical stimulation signal from the plurality of electrical stimulation signals based on the selected ERNA signal, and determine parameters of the determined electrical stimulation signal. In some examples, to determine parameters for the therapeutic electrical stimulation signal, the processing circuitry may be configured to determine parameters for the therapeutic electrical stimulation signal based on the determined parameters of the determined electrical stimulation signal.

The processing circuitry may output information indicative of the determined at least one parameter (810). In some examples, the processing circuitry may be configured to control stimulation generation circuitry 202 to deliver the therapeutic electrical stimulation signal based on the determined at least one parameter.

FIGS. 9A-9G are graphs illustrating ERNA signals generated with electrical stimulation delivered across one set of electrodes and sensed across different sets of electrodes. FIGS. 9A-9G illustrate examples of processing circuitry 210 receiving ERNA signals sensed on a plurality of electrodes (e.g., each one of FIGS. 9A-9G show ERNA signals from different pairs of electrodes). Processing circuitry 210 may select at least one electrode for sensing ERNA signals based on the sensed respective ERNA signals. For instance, processing circuitry 210 may select one of the electrodes based on ERNA signals shown in FIGS. 9A-9G (e.g., processing circuitry 210 may select electrode E3 (e.g., electrode 502A) based on FIG. 9A, select electrode E2*a*, which is part of group of electrodes 502B based on FIG. 9B, and so forth. Processing circuitry 210 may then determine the respective ERNA signals that are utilized for determining therapeutic electrical stimulation signals based on the selected at least one electrode.

There may be various factors that processing circuitry 210 may use to select at least one electrode for sensing ERNA signals based on the respective ERNA signals shown in FIGS. 9A-9G. As one example, processing circuitry 210 may determine which ERNA signal has the greatest amplitude (e.g., FIG. 9F). In this example, electrode E1*b*, which is one of group of electrodes 502C, has the highest amplitude ERNA signal. Processing circuitry 210 may then sense ERNA signal from electrode E1*b*, relative to housing of IMD 106, for determining parameters for the therapeutic electrical stimulation signal.

For instance, in the example of FIGS. 9A-9G, the processing circuitry (e.g., processing circuitry 210, as one non-limiting example) may have determined that the LFP measurements between electrode E1*c* and the electrode on the housing of IMD 106 is the highest. As shown in FIG. 5A, electrode E1*c* is in level E1 and is part of group of electrodes 502C. Processing circuitry 210 may output a stimulation signal via electrode E1*c* and the housing electrode, and sense the ERNA on different electrodes shown in FIGS. 9A-9G. The parameters for the stimulation signal may be 130 Hz, with 0.5 mA amplitude.

Accordingly, in the example of FIGS. 9A-9G, assume that processing circuitry 210 selected electrode E1*b* for sensing and selected electrode E1*c* for stimulation (e.g., determined electrode E1*c* for delivering therapeutic electrical stimulation signal based on the LFP measurements). In such an example, processing circuitry 210 may control stimulation generation circuitry 202 to deliver a plurality of electrical stimulation signals via the determined one or more electrodes (e.g., electrode E1*c* and IMD 106 housing electrode), where the plurality of electrical stimulation signals each comprise at least one different therapy parameter. For respective ones of the plurality of electrical stimulation signals, processing circuitry 210 may determine respective evoked resonant neural activity (ERNA) signals as sensed by electrode E1*b*, where the respective ERNA signals are evoked by delivery of the respective plurality of electrical stimulation signals.

Figure 9A:
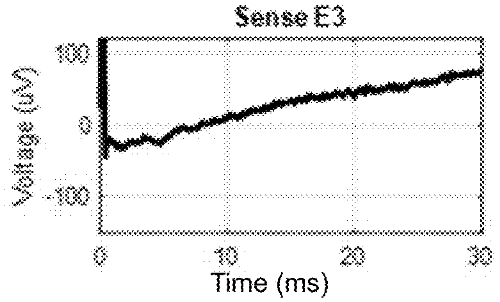
FIGS. 9A-9G are graphs illustrating ERNA signals generated with electrical stimulation delivered across one set of electrodes and sensed across different sets of electrodes.
Figure 9B:
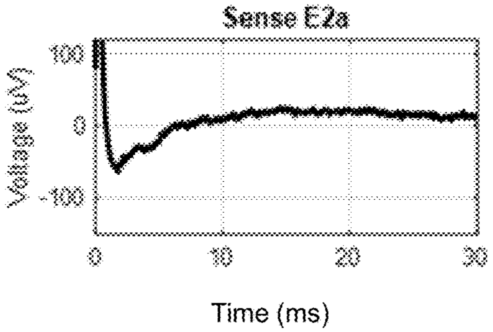
Figure 9C:
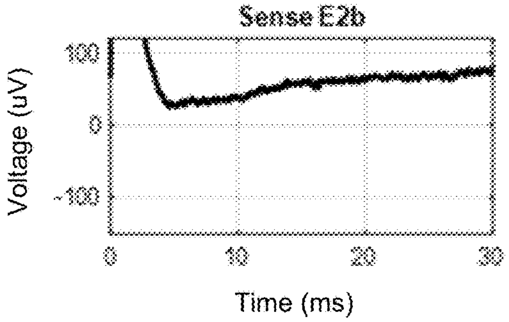
Figure 9D:
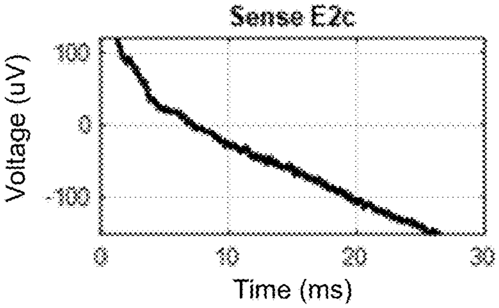
Figure 9E:
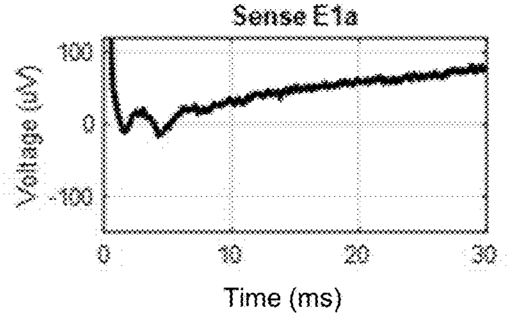
Figure 9F:
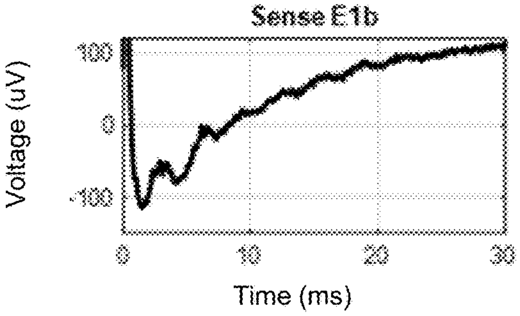
Figure 9G:
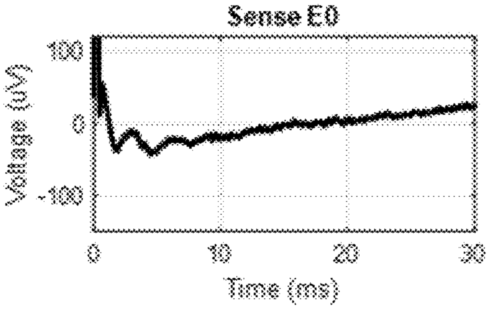

FIG. 9A illustrates the ERNA sensed from electrode E3 (e.g., electrode 502A) and the housing of IMD 106. FIG. 9B illustrates the ERNA sensed from electrode E2*a* (e.g., an electrode of group of electrodes 502B) and the housing of IMD 106. FIG. 9C illustrates the ERNA sensed from electrode E2*b* (e.g., an electrode of group of electrodes 502B) and the housing of IMD 106. FIG. 9D illustrates the ERNA sensed from electrode E2*c* (e.g., an electrode of group of electrodes 502B) and the housing of IMD 106. FIG. 9E illustrates the ERNA sensed from electrode E1*a* (e.g., an electrode of group of electrodes 502C) and the housing of IMD 106. FIG. 9F illustrates the ERNA sensed from electrode E1*b* (e.g., an electrode of group of electrodes 502C) and the housing of IMD 106. FIG. 9G illustrates the ERNA sensed from electrode E0 (e.g., electrode 502D) and the housing of IMD 106.

FIGS. 10A-10F are graphs illustrating ERNA signals generated with electrical stimulation delivered across different sets of electrodes and sensed across one set of electrodes. In one or more of examples described above, processing circuitry 210 may determine which electrodes to use for delivering therapeutic electrical stimulation signals based on LFP measurements. However, the example techniques are not so limited. In some examples, processing circuitry 210 may deliver electrical stimulation for evoking an ERNA signal across different sets of electrodes, and determine which electrodes to use for delivering the therapeutic electrical stimulation.

Figure 10A:
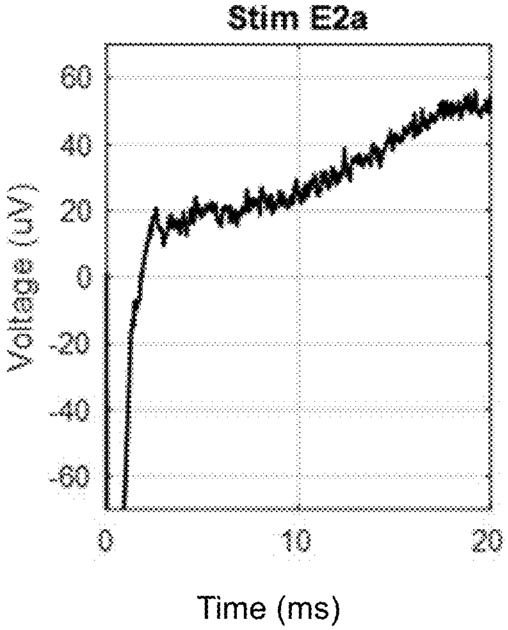
FIGS. 10A-10F are graphs illustrating ERNA signals generated with electrical stimulation delivered across different sets of electrodes and sensed across one set of electrodes.
Figure 10B:
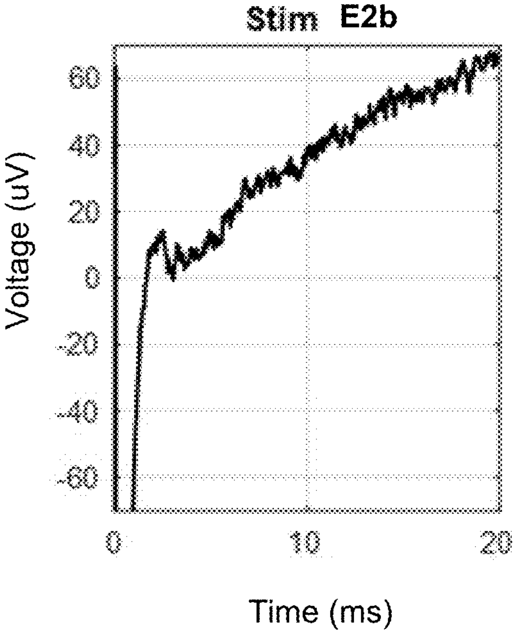
Figure 10C:
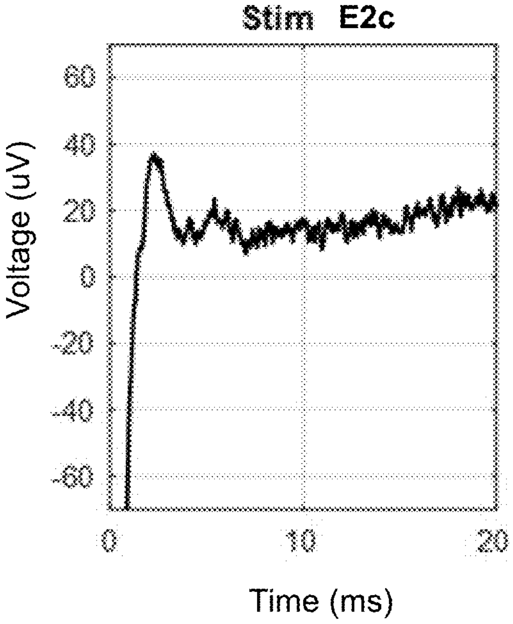
Figure 10D:
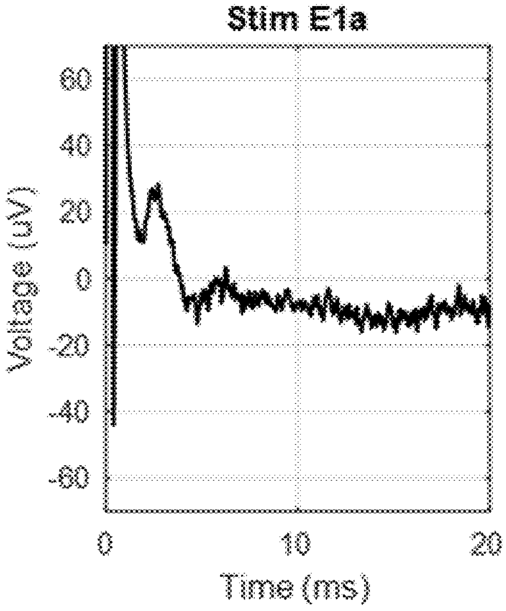
Figure 10E:
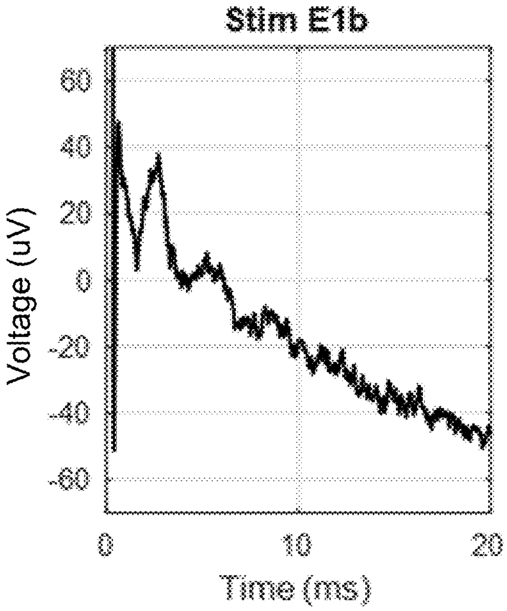
Figure 10F:
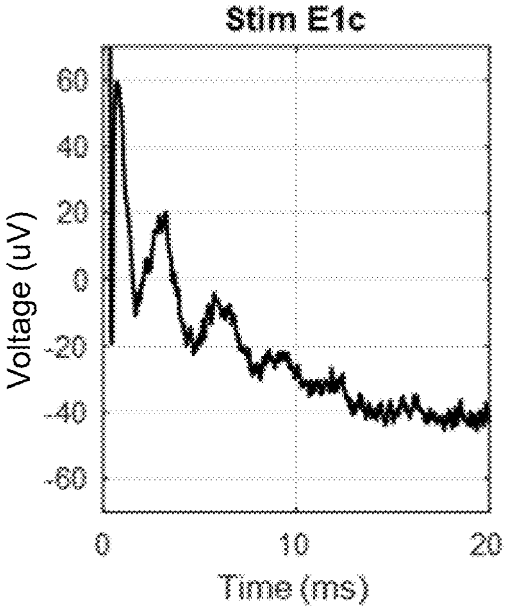

In FIGS. 10A-10F, the sensing electrodes are electrodes E0 (e.g., electrode 502D) and E3 (e.g., electrode 502A). FIG. 10A illustrates the ERNA signal sensed across electrodes E0 and E3 when stimulation to evoke an ERNA signal is delivered by electrode E2*a* (e.g., one of group of electrodes 502B) relative to the housing of IMD 106. FIG. 10B illustrates the ERNA signal sensed across electrodes E0 and E3 when stimulation to evoke an ERNA signal is delivered by electrode E2*b* (e.g., one of group of electrodes 502B) relative to the housing of IMD 106. FIG. 10C illustrates the ERNA signal sensed across electrodes E0 and E3 when stimulation to evoke an ERNA signal is delivered by electrode E2*c* (e.g., one of group of electrodes 502B) relative to the housing of IMD 106. FIG. 10D illustrates the ERNA signal sensed across electrodes E0 and E3 when stimulation to evoke an ERNA signal is delivered by electrode E1*a* (e.g., one of group of electrodes 502C) relative to the housing of IMD 106. FIG. 10E illustrates the ERNA signal sensed across electrodes E0 and E3 when stimulation to evoke an ERNA signal is delivered by electrode E1*b* (e.g., one of group of electrodes 502C) relative to the housing of IMD 106. FIG. 10F illustrates the ERNA signal sensed across electrodes E0 and E3 when stimulation to evoke an ERNA signal is delivered by electrode E1*c* (e.g., one of group of electrodes 502C) relative to the housing of IMD 106.

In the example of FIGS. 10A-10F, the ERNA signal evoked from stimulation on electrode E1*c*, and the ERNA signal evoked from stimulation on electrode E2*c* may exhibit the greatest amount of resonance, relative to the other signals. Accordingly, in some examples, the signal source of the LFP may be between electrode E1*c* and electrode E2*c*. In such examples, processing circuitry 210 may select at least one of E1*c* or E2*c*, or possibly both for bipolar stimulation, for delivering the therapeutic electrical stimulation signals.

The following describes one or more examples that may be performed separately or in various combinations in accordance with techniques described in this disclosure.

Example 1. A system for therapy parameter determination, the system comprising: memory; and processing circuitry coupled to the memory and configured to: determine a plurality of local field potential (LFP) measurements of an LFP, each of the LFP measurements measured with different electrodes implantable within a brain of a patient, wherein the LFP is intrinsically generated by a signal source within the brain of the patient; determine one or more electrodes for delivering therapeutic electrical stimulation signal based on the LFP measurements; control stimulation generation circuitry to deliver a plurality of electrical stimulation signals via the determined one or more electrodes, wherein the plurality of electrical stimulation signals each comprise at least one different therapy parameter; for each of the plurality of electrical stimulation signals, determine respective evoked resonant neural activity (ERNA) signals, wherein the respective ERNA signals are evoked by delivery of the respective plurality of electrical stimulation signals; determine parameters for the therapeutic electrical stimulation signal based on the respective ERNA signals; and output information indicative of the determined parameters.

Example 2. The system of example 1, wherein to control the stimulation generation circuitry to deliver the plurality of electrical stimulation signals via the determined one or more electrodes, the processing circuitry is configured to control the stimulation generation circuitry to deliver the plurality of electrical stimulation signals via the determined one or more electrodes, wherein a frequency for each of the plurality of electrical stimulation signals is within a range of frequencies.

Example 3. The system of example 2, wherein the range of frequencies is from 100 Hz to 220 Hz.

Example 4. The system of any of examples 1-3, wherein the processing circuitry is configured to: select an ERNA signal from the respective ERNA signals based on resonant activity of the respective ERNA signals; determine an electrical stimulation signal from the plurality of electrical stimulation signals based on the selected ERNA signal; and determine parameters of the determined electrical stimulation signal, wherein to determine parameters for the therapeutic electrical stimulation signal, the processing circuitry is configured to determine parameters for the therapeutic electrical stimulation signal based on the determined parameters of the determined electrical stimulation signal.

Example 5. The system of example 4, wherein the resonant activity of the respective ERNA signals includes one or more of peak-to-trough amplitude, time between peak-to-peak, change in peak amplitudes, amount of oscillations, rise or fall times, and frequency shift from early resonance to late resonance of the respective ERNA signals.

Example 6. The system of any of examples 1-5, wherein to determine the one or more electrodes for delivering therapeutic electrical stimulation signal based on the LFP measurements, the processing circuitry is configured to: determine an LFP measurement from the plurality of LFP measurements having a highest powered signal in one or more of a 4-8 Hertz (Hz) band, 8-33 Hz band, or 35-100 Hz band; and determine the one or more electrodes based on the LFP measurement having the highest powered signal in the 4-8 Hz band, 8-33 Hz band, or 35-100 Hz band.

Example 7. The system of any of examples 1-6, wherein to determine respective ERNA signals, the processing circuitry is configured to: receive respective ERNA signals sensed on a plurality of electrodes; select at least one electrode for sensing ERNA signals based on the sensed respective ERNA signals; and determine the respective ERNA signals from the selected at least one electrode.

Example 8. The system of any of examples 1-7, wherein to determine parameters for the therapeutic electrical stimulation signal, the processing circuitry is configured to determine parameters for the therapeutic electrical stimulation signal based on the respective ERNA signals and the LFP.

Example 9. The system of any of examples 1-8, wherein the processing circuitry is configured to control the stimulation generation circuitry to deliver the therapeutic electrical stimulation signal based on the determined parameters.

Example 10. The system of any of examples 1-9, further comprising an implantable medical device (IMD), wherein the IMD includes the processing circuitry.

Example 11. The system of any of examples 1-9, further comprising a programmer, wherein the programmer includes the processing circuitry.

Example 12. The system of any of examples 1-9, further comprising an implantable medical device (IMD) and a programmer, and wherein the processing circuitry is part of the IMD, the programmer, or both the IMD and the programmer.

Example 13. A method for therapy parameter determination, the method comprising: determining a plurality of local field potential (LFP) measurements of an LFP, each of the LFP measurements measured with different electrodes implantable within a brain of a patient, wherein the LFP is intrinsically generated by a signal source within the brain of the patient; determining one or more electrodes for delivering therapeutic electrical stimulation signal based on the LFP measurements; controlling stimulation generation circuitry to deliver a plurality of electrical stimulation signals via the determined one or more electrodes, wherein the plurality of electrical stimulation signals each comprise at least one different therapy parameter; for each of the plurality of electrical stimulation signals, determining respective evoked resonant neural activity (ERNA) signals, wherein the respective ERNA signals are evoked by delivery of the respective plurality of electrical stimulation signals; determining parameters for the therapeutic electrical stimulation signal based on the respective ERNA signals; and outputting information indicative of the determined parameters.

Example 14. The method of example 13, wherein controlling the stimulation generation circuitry to deliver the plurality of electrical stimulation signals via the determined one or more electrodes comprises controlling the stimulation generation circuitry to deliver the plurality of electrical stimulation signals via the determined one or more electrodes, wherein a frequency for each of the plurality of electrical stimulation signals is within a range of frequencies.

Example 15. The method of example 14, wherein the range of frequencies is from 100 Hz to 220 Hz.

Example 16. The method of any of examples 13-15, further comprising: selecting an ERNA signal from the respective ERNA signals based on resonant activity of the respective ERNA signals; determining an electrical stimulation signal from the plurality of electrical stimulation signals based on the selected ERNA signal; and determining parameters of the determined electrical stimulation signal, wherein determining parameters for the therapeutic electrical stimulation signal comprises determining parameters for the therapeutic electrical stimulation signal based on the determined parameters of the determined electrical stimulation signal.

Example 17. The method of example 16, wherein the resonant activity of the respective ERNA signals includes one or more of peak-to-trough amplitude, time between peak-to-peak, change in peak amplitudes, amount of oscillations, rise or fall times, and frequency shift from early resonance to late resonance of the respective ERNA signals.

Example 18. The method of any of examples 13-17, wherein determining the one or more electrodes for delivering therapeutic electrical stimulation signal based on the LFP measurements comprises: determining an LFP measurement from the plurality of LFP measurements having a highest powered signal in one or more of a 4-8 Hertz (Hz) band, 8-33 Hz band, or 35-100 Hz band; and determining the one or more electrodes based on the LFP measurement having the highest powered signal in the 4-8 Hz band, 8-33 Hz band, or 35-100 Hz band.

Example 19. The method of any of examples 13-18, wherein determining respective ERNA signals comprises: receiving respective ERNA signals sensed on a plurality of electrodes; selecting at least one electrode for sensing ERNA signals based on the sensed respective ERNA signals; and determining the respective ERNA signals from the selected at least one electrode.

Example 20. The method of any of examples 13-19, wherein determining parameters for the therapeutic electrical stimulation signal comprises determining parameters for the therapeutic electrical stimulation signal based on the respective ERNA signals and the LFP.

Example 21. The method of any of examples 13-20, further comprising controlling the stimulation generation circuitry to deliver the therapeutic electrical stimulation signal based on the determined parameters.

Example 22. The method of any of examples 13-21, wherein an implantable medical device (IMD) is configured to perform the method of any of examples 13-21.

Example 23. The method of any of examples 13-21, wherein a programmer is configured to perform the method of any of examples 13-21.

Example 24. The method of any of examples 13-21, wherein an implantable medical device (IMD), a programmer, or both the IMD and the programmer are configured to perform the method of any of examples 13-21.

Example 25. A computer-readable storage medium storing instructions thereon that when executed cause one or more processors to: determine a plurality of local field potential (LFP) measurements of an LFP, each of the LFP measurements measured with different electrodes implantable within a brain of a patient, wherein the LFP is intrinsically generated by a signal source within the brain of the patient; determine one or more electrodes for delivering therapeutic electrical stimulation signal based on the LFP measurements; control stimulation generation circuitry to deliver a plurality of electrical stimulation signals via the determined one or more electrodes, wherein the plurality of electrical stimulation signals each comprise at least one different therapy parameter; for each of the plurality of electrical stimulation signals, determine respective evoked resonant neural activity (ERNA) signals, wherein the respective ERNA signals are evoked by delivery of the respective plurality of electrical stimulation signals; determine parameters for the therapeutic electrical stimulation signal based on the respective ERNA signals; and output information indicative of the determined parameters.

Example 26. The computer-readable storage medium of example 25, further comprising instructions that cause the one or more processors to perform the method of any of examples 14-24.

Example 27. A system for therapy parameter determination, the system comprising: means for determining a plurality of local field potential (LFP) measurements of an LFP, each of the LFP measurements measured with different electrodes implantable within a brain of a patient, wherein the LFP is intrinsically generated by a signal source within the brain of the patient; means for determining one or more electrodes for delivering therapeutic electrical stimulation signal based on the LFP measurements; means for controlling stimulation generation circuitry to deliver a plurality of electrical stimulation signals via the determined one or more electrodes, wherein the plurality of electrical stimulation signals each comprise at least one different therapy parameter; means for determining respective evoked resonant neural activity (ERNA) signals for each of the plurality of electrical stimulation signals, wherein the respective ERNA signals are evoked by delivery of the respective plurality of electrical stimulation signals; means for determining parameters for the therapeutic electrical stimulation signal based on the respective ERNA signals; and means for outputting information indicative of the determined parameters.

Example 28. The system of example 27, further comprising means for performing the method of any of examples 14-24.

Example 1A. A system for therapy parameter determination, the system comprising: memory; and processing circuitry coupled to the memory and configured to: determine a plurality of local field potential (LFP) measurements of an LFP, wherein the LFP is intrinsically generated by a signal source within a brain of a patient; determine one or more electrodes for delivering a therapeutic electrical stimulation signal based on the LFP measurements; control stimulation generation circuitry to deliver a plurality of electrical stimulation signals via the determined one or more electrodes, wherein the plurality of electrical stimulation signals each comprise at least one different therapy parameter; for respective ones of the plurality of electrical stimulation signals, determine respective evoked signals, wherein the respective evoked signals are evoked by delivery of the respective plurality of electrical stimulation signals; determine at least one parameter for the therapeutic electrical stimulation signal based on the respective evoked signals; and output information indicative of the determined at least one parameter.

Example 2A. The system of example 1A, wherein each of the LFP measurements is measured with different electrodes within the brain of the patient.

Example 3A. The system of any of examples 1A and 2A, wherein a frequency of each of the plurality of electrical stimulation signals is lower than a threshold frequency, wherein an amplitude or pulse width of a first electrical stimulation signal of the plurality of electrical stimulation signals is different than an amplitude or pulse width of a second electrical stimulation signal of the plurality of electrical stimulation signals, wherein the evoked signals are evoked potential signals, and wherein to determine at least one parameter for the therapeutic electrical stimulation signal, the processing circuitry is configured to determine at least one of an amplitude or pulse width for the therapeutic electrical stimulation signal based on the evoked potential signals.

Example 4A. The system of any of examples 1A and 2A, wherein a frequency of each of the plurality of electrical stimulation signals is higher than a threshold frequency, wherein an amplitude or pulse width of a first electrical stimulation signal of the plurality of electrical stimulation signals is different than an amplitude or pulse width of a second electrical stimulation signal of the plurality of electrical stimulation signals, wherein the evoked signals are evoked resonant neural activity (ERNA) signals, and wherein to determine at least one parameter for the therapeutic electrical stimulation signal, the processing circuitry is configured to determine at least one of an amplitude or pulse width for the therapeutic electrical stimulation signal based on the ERNA signals.

Example 5A. The system of any of examples 1A and 2A, wherein a frequency of each of the plurality of electrical stimulation signals is higher than a threshold frequency, wherein a frequency of a first electrical stimulation signal of the plurality of electrical stimulation signals is different than a frequency of a second electrical stimulation signal of the plurality of electrical stimulation signals, wherein the evoked signals are evoked resonant neural activity (ERNA) signals, and wherein to determine at least one parameter for the therapeutic electrical stimulation signal, the processing circuitry is configured to.

Example 6A. The system of any of examples 1A and 2A, wherein the plurality of electrical stimulation signals comprises a first plurality of electrical stimulation signals, wherein a frequency of each electrical stimulation signal of the first plurality of electrical stimulation signals is lower than a threshold frequency, wherein an amplitude of a first electrical stimulation signal of the first plurality of electrical stimulation signals is different than an amplitude of a second electrical stimulation signal of the first plurality of electrical stimulation signals, wherein the evoked signals are evoked potential signals, wherein the processing circuitry is configured to: control the stimulation generation circuitry to deliver a second plurality of electrical stimulation signals via the determined one or more electrodes, wherein a frequency of a first electrical stimulation signal of the second plurality of electrical stimulation signals is different than a frequency of a second electrical stimulation signal of the second plurality of electrical stimulation signals; for respective ones of the second plurality of electrical stimulation signals, determine respective evoked resonant neural activity (ERNA) signals, wherein the respective ERNA signals are evoked by delivery of the respective second plurality of electrical stimulation signals, wherein to determine at least one parameter for the therapeutic electrical stimulation signal based on the respective evoked signals, the processing circuitry is configured to determine at least one of an amplitude or pulse width of the therapeutic electrical stimulation signal based on the evoked potential signals, and determine a frequency of the therapeutic electrical stimulation signal based on the ERNA signals.

Example 7A. The system of any of examples 1A-6A, wherein the evoked signals are evoked potential signals, and wherein the processing circuitry is configured to: select an evoked potential signal from the respective evoked potential signals based on at least one of amplitude, peak latency, or trough latency of the respective evoked potential signals; determine an electrical stimulation signal from the plurality of electrical stimulation signals based on the selected evoked potential signal; and determine parameters of the determined electrical stimulation signal, wherein to determine at least one parameter for the therapeutic electrical stimulation signal, the processing circuitry is configured to determine at least one parameter for the therapeutic electrical stimulation signal based on the determined parameters of the determined electrical stimulation signal.

Example 8A. The system of any of examples 1A-7A, wherein the evoked signals are evoked resonant neural activity (ERNA) signals, and wherein the processing circuitry is configured to: select an ERNA signal from the respective ERNA signals based on resonant activity of the respective ERNA signals; determine an electrical stimulation signal from the plurality of electrical stimulation signals based on the selected ERNA signal; and determine parameters of the determined electrical stimulation signal, wherein to determine at least one parameter for the therapeutic electrical stimulation signal, the processing circuitry is configured to determine at least one parameter for the therapeutic electrical stimulation signal based on the determined parameters of the determined electrical stimulation signal.

Example 9A. The system of example 8A, wherein the resonant activity of the respective ERNA signals includes one or more of peak-to-trough amplitude, time between peak-to-peak, change in peak amplitudes, amount of oscillations, rise or fall times, and frequency shift from early resonance to late resonance of the respective ERNA signals.

Example 10A. The system of any of examples 1A-9A, wherein to determine the one or more electrodes for delivering therapeutic electrical stimulation signal based on the LFP measurements, the processing circuitry is configured to: determine an LFP measurement from the plurality of LFP measurements having a highest powered signal in one or more of a 4-8 Hertz (Hz) band, 8-33 Hz band, or 35-100 Hz band; and determine the one or more electrodes based on the LFP measurement having the highest powered signal in the 4-8 Hz band, 8-33 Hz band, or 35-100 Hz band.

Example 11A. The system of any of examples 1A-10A, wherein to determine respective evoked signals, the processing circuitry is configured to: receive respective evoked signals sensed on a plurality of electrodes; select at least one electrode for sensing the evoked signals based on the sensed respective evoked signals; and determine the respective evoked signals from the selected at least one electrode.

Example 12A. The system of any of examples 1A-11A, wherein the processing circuitry is configured to control the stimulation generation circuitry to deliver the therapeutic electrical stimulation signal based on the determined at least one parameter.

Example 13A. The system of any of examples 1A-12A, further comprising an implantable medical device (IMD), wherein the IMD includes the processing circuitry.

Example 14A. The system of any of examples 1A-12A, further comprising an implantable medical device (IMD) and a programmer, and wherein the processing circuitry is part of the IMD, the programmer, or both the IMD and the programmer.

Example 15A. A method for therapy parameter determination, the method comprising: determining a plurality of local field potential (LFP) measurements of an LFP, wherein the LFP is intrinsically generated by a signal source within a brain of a patient; determining one or more electrodes for delivering a therapeutic electrical stimulation signal based on the LFP measurements; controlling stimulation generation circuitry to deliver a plurality of electrical stimulation signals via the determined one or more electrodes, wherein the plurality of electrical stimulation signals each comprise at least one different therapy parameter; for respective ones of the plurality of electrical stimulation signals, determining respective evoked signals, wherein the respective evoked signals are evoked by delivery of the respective plurality of electrical stimulation signals; determining at least one parameter for the therapeutic electrical stimulation signal based on the respective evoked signals; and outputting information indicative of the determined at least one parameter.

Example 16A. The method of example 15A, wherein each of the LFP measurements is measured with different electrodes implantable within the brain of the patient.

Example 17A. The method of any of examples 15A and 16A, wherein a frequency of each of the plurality of electrical stimulation signals is lower than a threshold frequency, wherein an amplitude or pulse width of a first electrical stimulation signal of the plurality of electrical stimulation signals is different than an amplitude or pulse width of a second electrical stimulation signal of the plurality of electrical stimulation signals, wherein the evoked signals are evoked potential signals, and wherein determining at least one parameter for the therapeutic electrical stimulation signal comprises determining at least one of an amplitude or pulse width for the therapeutic electrical stimulation signal based on the evoked potential signals.

Example 18A. The method of any of examples 15A and 16A, wherein a frequency of each of the plurality of electrical stimulation signals is higher than a threshold frequency, wherein an amplitude or pulse width of a first electrical stimulation signal of the plurality of electrical stimulation signals is different than an amplitude or pulse width of a second electrical stimulation signal of the plurality of electrical stimulation signals, wherein the evoked signals are evoked resonant neural activity (ERNA) signals, and wherein determining at least one parameter for the therapeutic electrical stimulation signal comprises determining at least one of an amplitude or pulse width for the therapeutic electrical stimulation signal based on the ERNA signals.

Example 19A. The method of any of examples 15A and 16A, wherein a frequency of each of the plurality of electrical stimulation signals is higher than a threshold frequency, wherein a frequency of a first electrical stimulation signal of the plurality of electrical stimulation signals is different than a frequency of a second electrical stimulation signal of the plurality of electrical stimulation signals, wherein the evoked signals are evoked resonant neural activity (ERNA) signals, and wherein determining at least one parameter for the therapeutic electrical stimulation signal comprises determining a frequency for the therapeutic electrical stimulation signal based on the ERNA signals.

Example 20A. A method comprising performing the operations of any of examples 1A-14A.

Example 21A. A computer-readable storage medium storing instructions thereon that when executed cause one or more processors to: determine a plurality of local field potential (LFP) measurements of an LFP, wherein the LFP is intrinsically generated by a signal source within a brain of a patient; determine one or more electrodes for delivering a therapeutic electrical stimulation signal based on the LFP measurements; control stimulation generation circuitry to deliver a plurality of electrical stimulation signals via the determined one or more electrodes, wherein the plurality of electrical stimulation signals each comprise at least one different therapy parameter; for respective ones of the plurality of electrical stimulation signals, determine respective evoked signals, wherein the respective evoked signals are evoked by delivery of the respective plurality of electrical stimulation signals; determine at least one parameter for the therapeutic electrical stimulation signal based on the respective evoked signals; and output information indicative of the determined at least one parameter.

Example 22A. The computer-readable storage medium of example 20A further comprising instructions that cause the one or more processors to perform the method of any of examples 15A-19A or the operations of the features of any of examples 2A-14A.

Example 23A. A system comprising means for performing the method of any of examples 15A-19A or the operations of the features of any of examples 1A-14A.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A system for therapy parameter determination, the system comprising:
memory; and
processing circuitry coupled to the memory and configured to:
deliver, with stimulation generation circuitry, a first plurality of electrical stimulation signals, wherein a frequency of each electrical stimulation signal of the first plurality of electrical stimulation signals is lower than a threshold frequency, and an amplitude or pulse width of a first electrical stimulation signal of the first plurality of electrical stimulation signals is different than an amplitude or pulse width of a second electrical stimulation signal of the first plurality of electrical stimulation signals, and wherein delivery of each of the first plurality of electrical stimulation signals evokes a respective evoked potential signal of a plurality of evoked potential signals;
deliver, with the stimulation generation circuitry, a second plurality of electrical stimulation signals, wherein a frequency of a first electrical stimulation signal of the second plurality of electrical stimulation signals is different than a frequency of a second electrical stimulation signal of the second plurality of electrical stimulation signals, and wherein delivery of each of the second plurality of electrical stimulation signals evokes a respective evoked resonant neural activity (ERNA) signal of a plurality of ERNA signals;
determine at least one of an amplitude or pulse width of a therapeutic electrical stimulation signal and a frequency of the therapeutic electrical stimulation signal, wherein the amplitude or pulse width of the therapeutic electrical stimulation signal is determined based on the evoked potential signals, and wherein the frequency of the therapeutic electrical stimulation signal is determined based on the ERNA signals; and
deliver, with the stimulation generation circuitry, the therapeutic electrical stimulation signal.

2. The system of claim 1, wherein the processing circuitry is configured to determine a plurality of local field potential (LFP) measurements of an LFP, wherein the LFP is intrinsically generated by a signal source within a brain of a patient, and wherein to determine the plurality of LFP measurements, the processing circuitry is configured to receive each of the LFP measurements as measured with different electrodes implantable within the brain of the patient.

3. The system of claim 1,
wherein to deliver the second plurality of electrical stimulation signals, the processing circuitry is configured to deliver, with the stimulation generation circuitry, the second plurality of stimulation signals having characteristics that a frequency of each of the plurality of electrical stimulation signals is higher than the threshold frequency.

4. The system of claim 1, wherein the processing circuitry is configured to:
select an evoked potential signal from the plurality of evoked potential signals based on at least one of amplitude, peak latency, or trough latency of the evoked potential signals, wherein delivery of one of the first plurality of electrical stimulation signals evoked the selected evoked potential signal; and
determine parameters of the one of the first plurality of electrical stimulation signals that evoked the selected evoked potential signal,
wherein to determine at least one of the amplitude or pulse width of the therapeutic electrical stimulation signal, the processing circuitry is configured to determine at least one of the amplitude or pulse width of the therapeutic electrical stimulation signal based on the determined parameters of the one of the first plurality of electrical stimulation signals that evoked the selected evoked potential signal.

5. The system of claim 1, wherein the processing circuitry is configured to:
select an ERNA signal from the plurality of ERNA signals based on resonant activity of the ERNA signals, wherein delivery of one of the second plurality of electrical stimulation signals evoked the selected ERNA; and
determine parameters of the one of the second plurality of electrical stimulation signals that evoked the selected ERNA,
wherein to determine the frequency of the therapeutic electrical stimulation signal, the processing circuitry is configured to determine the frequency of the therapeutic electrical stimulation signal based on the determined parameters of the one of the second plurality of electrical stimulation signals that evoked the selected ERNA.

6. The system of claim 5, wherein the resonant activity of the ERNA signals includes one or more of peak-to-trough amplitude, time between peak-to-peak, change in peak amplitudes, amount of oscillations, rise or fall times, and frequency shift from early resonance to late resonance of the ERNA signals.

7. The system of claim 2, wherein the processing circuitry is configured to determine one or more electrodes for delivering the therapeutic electrical stimulation signal based on the LFP measurements, and wherein to determine the one or more electrodes for delivering the therapeutic electrical stimulation signal based on the LFP measurements, the processing circuitry is configured to:

determine an LFP measurement from the plurality of LFP measurements having a highest powered signal in one or more of a 4-8 Hertz (Hz) band, 8-33 Hz band, or 35-100 Hz band; and determine the one or more electrodes based on the LFP measurement having the highest powered signal in the 4-8 Hz band, 8-33 Hz band, or 35-100 Hz band.

8. The system of claim 1, wherein to the processing circuitry is configured to:

select at least one electrode from which to receive the evoked potential signals and the ERNA signals.

9. The system of claim 1, wherein the processing circuitry is configured to control the stimulation generation circuitry to deliver the therapeutic electrical stimulation signal.

10. The system of claim 1, further comprising an implantable medical device (IMD), wherein the IMD includes the processing circuitry.

11. The system of claim 1, further comprising an implantable medical device (IMD) and a programmer, and wherein the processing circuitry is part of the IMD, the programmer, or both the IMD and the programmer.

12. The system of claim 1, wherein the processing circuitry is configured to receive information indicative of one or more electrodes used for delivering the therapeutic electrical stimulation signal.

13. The system of claim 1, wherein to determine the amplitude, pulse width, or frequency of the therapeutic electrical stimulation signal, the processing circuitry is configured to receive information indicative of the amplitude, pulse width, or frequency of the therapeutic electrical stimulation signal.

14. The system of claim 2, further comprising an implantable medical device (IMD), the IMD comprising the processing circuitry, wherein the processing circuitry is configured to determine one or more electrodes for delivering the therapeutic electrical stimulation signal based on the LFP measurements, and wherein to determine the one or more electrodes, the processing circuitry is configured to determine the one or more electrodes based on the LFP measurement being an input to the processing circuitry.

15. The system of claim 1, further comprising an implantable medical device (IMD), the IMD comprising the processing circuitry, and wherein to determine the at least one of the amplitude or pulse width of the therapeutic electrical stimulation signal and the frequency of the therapeutic electrical stimulation signal, the processing circuitry is configured to determine the at least one of the amplitude or pulse width of the therapeutic electrical stimulation signal and the frequency of the therapeutic electrical stimulation signal based on the evoked potential signals and the ERNA signals being input to the processing circuitry.

16. A method for therapy parameter determination, the method comprising:

delivering, with stimulation generation circuitry, a first plurality of electrical stimulation signals, wherein a frequency of each electrical stimulation signal of the first plurality of electrical stimulation signals is lower than a threshold frequency, and an amplitude or pulse width of a first electrical stimulation signal of the first plurality of electrical stimulation signals is different than an amplitude or pulse width of a second electrical stimulation signal of the first plurality of electrical stimulation signals, and wherein delivery of each of the first plurality of electrical stimulation signals evokes a respective evoked potential signal of a plurality of evoked potential signals;

delivering, with the stimulation generation circuitry, a second plurality of electrical stimulation signals, wherein a frequency of a first electrical stimulation signal of the second plurality of electrical stimulation signals is different than a frequency of a second electrical stimulation signal of the second plurality of electrical stimulation signals, and wherein delivery of each of the second plurality of electrical stimulation signals evokes a respective evoked resonant neural activity (ERNA) signal of a plurality of ERNA signals;

determining at least one of an amplitude or pulse width of a therapeutic electrical stimulation signal and a frequency of the therapeutic electrical stimulation signal, wherein the amplitude or pulse width of the therapeutic electrical stimulation signal is determined based on the evoked potential signals, and wherein the frequency of the therapeutic electrical stimulation signal is determined based on the ERNA signals; and delivering, with the stimulation generation circuitry, the therapeutic electrical stimulation signal.

17. The method of claim 16, further comprising determining a plurality of local field potential (LFP) measurements of an LFP, wherein the LFP is intrinsically generated by a signal source within a brain of a patient, and wherein determining the plurality of LFP measurements comprises receiving each of the LFP measurements as measured with different electrodes implantable within the brain of the patient.

18. The method of claim 16, wherein delivering the second plurality of electrical stimulation signals comprises delivering, with the stimulation generation circuitry, the second plurality of stimulation signals having characteristics that a frequency of each of the plurality of electrical stimulation signals is higher than the threshold frequency.

19. A computer-readable storage medium storing instructions thereon that when executed cause one or more processors to:

deliver, with stimulation generation circuitry, a first plurality of electrical stimulation signals, wherein a frequency of each electrical stimulation signal of the first plurality of electrical stimulation signals is lower than a threshold frequency, and an amplitude or pulse width of a first electrical stimulation signal of the first plurality of electrical stimulation signals is different than an amplitude or pulse width of a second electrical stimulation signal of the first plurality of electrical stimulation signals, and wherein delivery of each of the first plurality of electrical stimulation signals evokes a respective evoked potential signal of a plurality of evoked potential signals;

deliver, with the stimulation generation circuitry, a second plurality of electrical stimulation signals, wherein a frequency of a first electrical stimulation signal of the second plurality of electrical stimulation signals is different than a frequency of a second electrical stimulation signal of the second plurality of electrical stimulation signals, and wherein delivery of each of the second plurality of electrical stimulation signals evokes a respective evoked resonant neural activity (ERNA) signal of a plurality of ERNA signals;

determine at least one of an amplitude or pulse width of a therapeutic electrical stimulation signal and a frequency of the therapeutic electrical stimulation signal, wherein the amplitude or pulse width of the therapeutic electrical stimulation signal is determined based on the evoked potential signals, and wherein the frequency of the therapeutic electrical stimulation signal is determined based on the ERNA signals; and deliver, with the stimulation generation circuitry, the therapeutic electrical stimulation signal.

* * * * *